(12) United States Patent
Shimada et al.

(10) Patent No.: US 9,087,680 B2
(45) Date of Patent: Jul. 21, 2015

(54) ANALYSIS DEVICE, ANALYSIS METHOD, AND STORAGE MEDIUM

(75) Inventors: Haruo Shimada, Kanagawa (JP);
Yoshimasa Nakatani, Kanagawa (JP);
Yuka Morishita, Kanagawa (JP);
Kazumasa Kinoshita, Kanagawa (JP);
Tomohiro Sakuma, Tokyo (JP); Yasuto Yokoi, Tokyo (JP)

(73) Assignees: SHISEIDO COMPANY, LTD., Tokyo (JP); BIO CHROMATO, INC., Kanagawa (JP)

( * ) Notice: Subject to any disclaimer, the term of this patent is extended or adjusted under 35 U.S.C. 154(b) by 0 days.

(21) Appl. No.: 14/240,422

(22) PCT Filed: Aug. 30, 2012

(86) PCT No.: PCT/JP2012/071976
§ 371 (c)(1),
(2), (4) Date: Feb. 24, 2014

(87) PCT Pub. No.: WO2013/031881
PCT Pub. Date: Mar. 7, 2013

(65) Prior Publication Data
US 2014/0183353 A1    Jul. 3, 2014

(30) Foreign Application Priority Data

Sep. 2, 2011 (JP) ................................. 2011-191679
Aug. 20, 2012 (JP) ................................. 2012-181749

(51) Int. Cl.
*H01J 49/26* (2006.01)
*H01J 49/00* (2006.01)
*H01J 49/02* (2006.01)

(52) U.S. Cl.
CPC ........... *H01J 49/0036* (2013.01); *H01J 49/022* (2013.01)

(58) Field of Classification Search
USPC .......... 250/281, 282, 283; 702/22, 23, 24, 25, 702/26, 27, 28
See application file for complete search history.

(56) References Cited

U.S. PATENT DOCUMENTS

| 7,053,365 B2 | 5/2006 | Shimomura |
| 2011/0012016 A1* | 1/2011 | Maier et al. .................. 250/282 |
| 2011/0202282 A1 | 8/2011 | Kostrzewa |

FOREIGN PATENT DOCUMENTS

| JP | 03-165445 | 7/1991 |
| JP | 05-149935 | 6/1993 |

(Continued)

OTHER PUBLICATIONS

International Search Report mailed on Dec. 18, 2012.
(Continued)

*Primary Examiner* — Nicole Ippolito
(74) *Attorney, Agent, or Firm* — IPUSA, PLLC

(57) ABSTRACT

An analysis device includes a sample substance spectrum acquisition unit that acquires a plurality of sample substance spectra obtained a plurality of times for a sample substance; a storage unit that stores a plurality of reference spectra for a known substance; a first evaluation value calculation unit that calculates a first evaluation value for a combination of a sample substance spectrum and a reference spectrum extracted from the plurality of sample substance spectra and the plurality of reference spectra, the first evaluation value representing a similarity between a peak intensity ratio of the reference spectrum and a peak intensity ratio of a portion of the sample substance spectrum corresponding to a peak in the reference spectrum; and a second evaluation value calculation unit that calculates a second evaluation value representing a similarity between the sample substance and the known substance based on the first evaluation values for the combinations.

15 Claims, 29 Drawing Sheets

(56) References Cited

FOREIGN PATENT DOCUMENTS

| | | |
|---|---|---|
| JP | 09-043199 | 2/1997 |
| JP | 2004-251830 | 9/2004 |
| JP | 2005-127814 | 5/2005 |
| JP | 2005-274352 | 10/2005 |
| JP | 2010-256101 | 11/2010 |
| WO | WO 2006/106724 | 10/2006 |
| WO | 2011/015631 | 2/2011 |

OTHER PUBLICATIONS

Stein, S.E., & Scott, D.R. "Optimization and testing of mass spectral library search algorithms for compound identification." Journal of the American Society for Mass Spectrometry, 5(9), 859-866 (1994). oi: 10. 1016/1044-0305(94)87009-8.

Partial Supplementary European Search Report dated Apr. 23, 2015.

Imhoi Koo et al, "Comparison of Spectral Similarity Measures for Compound Identification" Bioinformatics and Biomedical Engineering, (ICBBE) 2011 5th International Conference on, IEEE, May 10, 2011, pp. 1-4, XP031878498.

Wan K X et al, "Comparing similar spectra: from similarity index to spectral contrast angle", Journal of the American Society for Mass Spectrometry, Elsevier Science Inc, US, vol. 13, No. 1, Jan. 1, 2002, pp. 85-88, XP004326927.

* cited by examiner

| DATA LABEL (m/z) | 200, 207, 248, 257 |
| --- | --- |
| DATA (INTENSITY) | (10, 7, 12, 23) |

The DATA (INTENSITY) row is labeled $I^*$.

|  | $S^*_{j1}$ | $S^*_{j2}$ | $S^*_{j3}$ | $S^*_{j4}$ | $S^*_{j5}$ |
|---|---|---|---|---|---|
| $S_1$ | 0.5 | 0.2 | 0.1 | 0.4 | 0.2 |
| $S_2$ | 0.1 | 0.8 | 0.8 | 0.3 | 0.1 |
| $S_3$ | 0.3 | 0.2 | 0.3 | 0.2 | 0.3 |
| $S_4$ | 0.1 | 0.3 | 0.2 | 0.6 | 0.2 |
| $S_5$ | 0.3 | 0.2 | 0.9 | 0.2 | 0.5 |
| $S_6$ | 0.1 | 0.5 | 0.1 | 0.2 | 0.5 |

FIG.10

|  | $S^*_{j1}$ | $S^*_{j2}$ | $S^*_{j3}$ | $S^*_{j4}$ | $S^*_{j5}$ |
|---|---|---|---|---|---|
| $S_1$ | 0.5 | 0.7 | 0.8 | 1.2 | 1.4 |
| $S_2$ | 0.5 | 1.3 | 2.1 | 2.4 | 2.5 |
| $S_3$ | 0.5 | 1.3 | 2.1 | 2.4 | 2.7 |
| $S_4$ | 0.5 | 1.3 | 2.1 | 2.7 | 2.9 |
| $S_5$ | 0.5 | 1.3 | 2.2 | 2.7 | 3.2 |
| $S_6$ | 0.5 | 1.3 | 2.2 | 2.7 | 3.2 |

FIG.15

| HIT NUMBER | SUBSTANCE IDENTIFIER | SUBSTANCE NAME | OVERALL SIMILARITY $V_j$ | EXPECTED VALUE $E_j$ | SPECTRUM NUMBER | INDIVIDUAL SPECTRUM SIMILARITY |
|---|---|---|---|---|---|---|
| 1 | LID | Lidocain | 0.537 | 0.000 | 0 | 0.537 |
| 2 | DIF_HCO60 | Diphenhydramine and HCO60 mixture | 0.215 | 0.000 | 0 | 0.238 |
|   |   |   |   |   | 1 | 0.192 |
| 3 | TocAce | Tocopherol acetate | 0.031 | 0.000 | 0 | 0.031 |
| 4 | EcoGum | EcoGum | 0.010 | 0.477 | 0 | 0.010 |
| 5 | Polypropylene | Polypropylene | 0.007 | 1.806 | 0 | 0.007 |
| 6 | Solanine | Solanine | 0.005 | 3.664 | 0 | 0.005 |
| 7 | Urea | Urea | 0.002 | 6.772 | 0 | 0.002 |
| 8 | Crotamiton | Crotamiton | 0.001 | 7.461 | 0 | 0.001 |
| 9 | Caffeine | Caffeine | 0.000 | 8.154 | 0 | 0.000 |
| 10 | Irganox1010 | Irganox1010 | 0.000 | 8.163 | 0 | 0.000 |

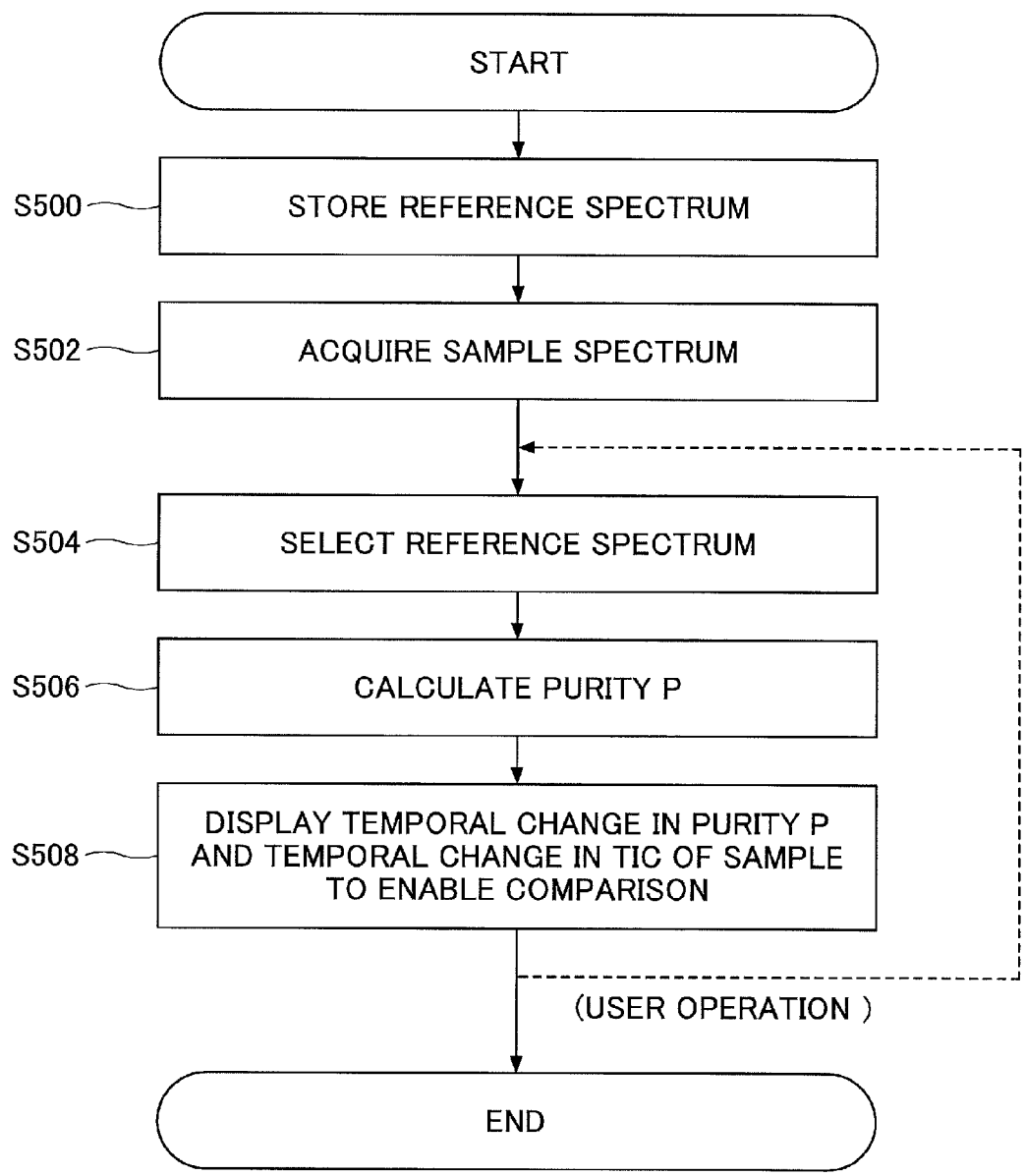

ANALYSIS DEVICE, ANALYSIS METHOD, AND STORAGE MEDIUM

TECHNICAL FIELD

The present disclosures relate to an analysis device, an analysis method, and a storage medium.

BACKGROUND ART

Mass spectrometers for detecting components of a sample substance are known. Various forms of research have been conducted with regard to methods for identifying a sample substance by analyzing a mass spectrum output by the mass spectrometer.

LC-MS (Liquid Chromatography Mass Spectrometer) and GC-MS (Gas Chromatography Mass Spectrometer) are generally used to separate a sample mixture into components through LC (liquid chromatography) or GC (gas chromatography) and obtain a mass spectrum of a single component through MS (mass spectrometry).

A mass spectrum of a single component may be compared with reference mass spectra that are pre-registered in a database, and by finding a matching spectrum from the database, a sample substance may be identified with relative ease.

Patent Document 1 discloses a chromatograph mass spectrometer that introduces a sample substance to a MS unit to acquire a mass spectrum and adjusts various types of parameters of the MS unit based on a target reference spectrum for the sample substance that is provided beforehand.

Non-Patent Literature Document 1 discloses a technique for identifying a sample substance by comparing a mass spectrum with reference spectra pre-registered in a database and finding a matching spectrum from the database.

PRIOR ART DOCUMENTS

Patent Documents

Patent Document 1: Japanese Laid-Open Patent Publication No. 2005-274352

Non-Patent Literature Documents

Non-Patent Literature Document 1: Stein, S. E., & Scott, D. R. (1994). Optimization and testing of mass spectral library search algorithms for compound identification. Journal of the American Society for Mass Spectrometry, 5(9), 859-866. oi: 10.1016/1044-0305(94)87009-8.

SUMMARY OF THE INVENTION

Problem to be Solved by the Invention

However, the conventional analysis technique merely involves analyzing the mass spectrum of a single component separated by the LC-MS or GC-MS, for example. That is, an analysis technique for analyzing a mass spectrum of multiple components has not been established.

As a result, time-consuming labor has been required for contemplating separation conditions for each sample substance, for example.

In recent years, techniques such as DART-MS (Direct Analysis in Real Time Mass Spectrometry) for directly acquiring a mass spectrum without performing separation (direct measurement technique) are becoming publicly known. DART-MS is advantageous in that it enables speedy measurement without requiring separation and allows measurement of substances such as plastic that cannot be dissolved by a solvent, for example.

However, because an analysis technique for analyzing a mass spectrum of multiple components has not been established, application of the direct measurement technique is limited to samples with predetermined analysis targets.

The present invention has been conceived in view of the foregoing problems associated with the prior art, and it is one object of the present invention to provide an analysis device that is capable of analyzing a mass spectrum of multiple components and using the analysis to identify a sample substance.

Means for Solving the Problem

According to one embodiment of the present invention, an analysis device is provided that includes a sample substance spectrum acquisition unit that acquires a plurality of sample substance spectra obtained a plurality of times for a same sample substance; a storage unit that stores a plurality of reference spectra for a known substance; a first evaluation value calculation unit that calculates a first evaluation value for a combination of a sample substance spectrum and a reference spectrum extracted from the plurality of sample substance spectra and the plurality of reference spectra, the first evaluation value representing a similarity between a peak intensity ratio of the reference spectrum and a peak intensity ratio of a portion of the sample substance spectrum corresponding to a peak in the reference spectrum; and a second evaluation value calculation unit that calculates a second evaluation value representing a similarity between the sample substance and the known substance based on the first evaluation values for a plurality of the combinations.

Advantageous Effect of the Invention

According to an aspect of the present invention, an analysis device may be provided that is capable of analyzing a mass spectrum of multiple components and identifying a sample substance with greater accuracy.

BRIEF DESCRIPTION OF THE DRAWINGS

FIG. 9 illustrates individual spectrum similarities calculated for a known substance expressed in the form of matrix data;

FIG. 10 illustrates partial total values calculated for each set of data;

FIG. 15 is a table indicating experiment and analysis results;

FIG. 27 is a flowchart illustrating process steps executed by the analysis device of the third embodiment.

EMBODIMENTS FOR IMPLEMENTING THE INVENTION

In the following, embodiments of the present invention are described with reference to the accompanying drawings.

<First Embodiment>

In the following, an analysis device 1 according to a first embodiment of the present invention is described with reference to the drawings.

[Basic Configuration]

Figure 1:
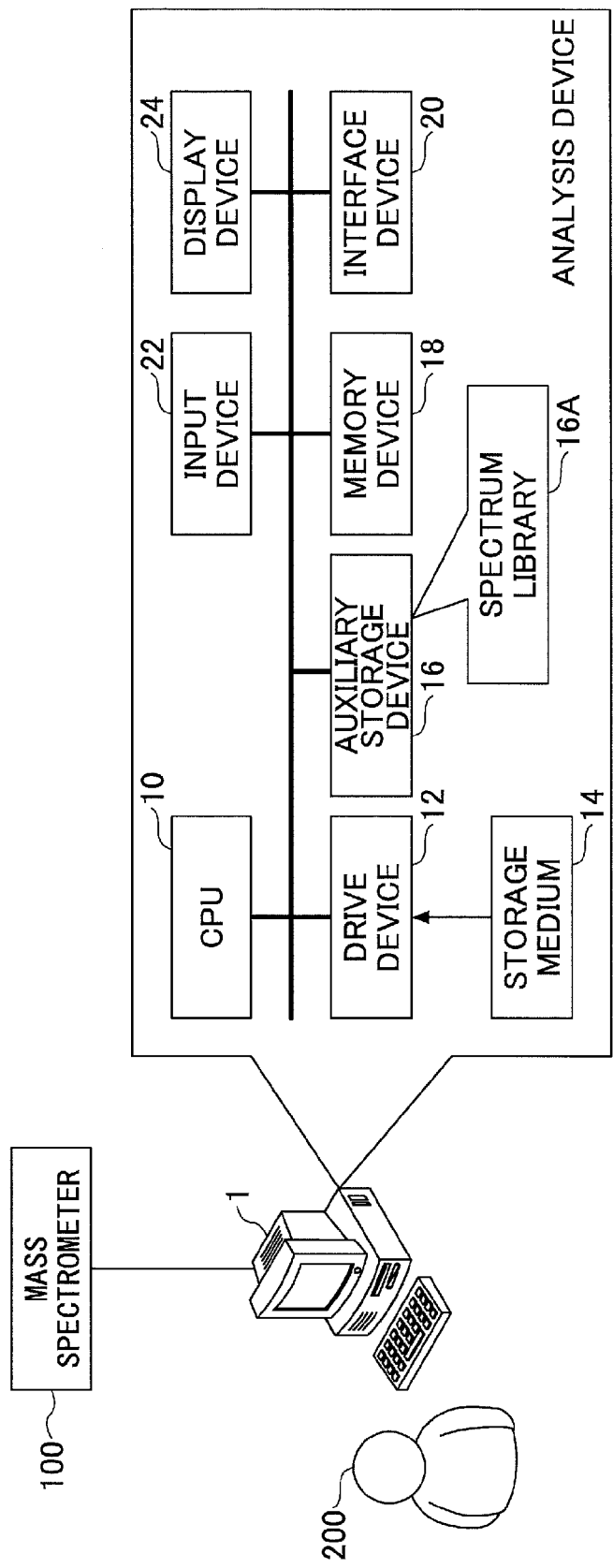
FIG. 1 illustrates an exemplary system configuration of an analysis device according to an embodiment of the present invention.

FIG. 1 illustrates an exemplary system configuration of the analysis device 1 according to the first embodiment. As illustrated in FIG. 1, the analysis device 1 is implemented by an information processing device such as a computer that is connected to a mass spectrometer 100. A user 200 may perform various operations such as entering settings and commands using the analysis device 1, for example.

The analysis device 1 includes a CPU (central processing unit) 10, a drive device 12, an auxiliary storage device 16, a memory device 18, an interface device 20, an input device 22, and a display device 24. These component elements may be interconnected via a bus or a serial line, for example.

The CPU 10 is a processor including a program counter, various computing units, a LSU (Load Store Unit), and a general-purpose register, for example. The drive device 12 is a device capable of reading a program or data from a storage medium 14. When the storage medium 14 storing a program is loaded into the drive device 12, the program may be installed into the auxiliary storage device 16 from the recording medium 14 via the drive device 12. The storage medium 14 is a portable recording medium such as a CD-ROM, a DVD, or a USB memory, for example. The auxiliary storage device 16 may be an EEPROM (Electronically Erasable and Programmable Read Only Memory), a ROM (Read Only Memory), a HDD (Hard Disk Drive), or a flash memory, for example.

A program may be installed using the storage medium 14 as described above, or alternatively, the interface device 20 may download a program from another computer via a network and install the downloaded program into the auxiliary storage device 16, for example. Also, the program may be stored in advance in the auxiliary storage device 16 at the time of shipment of the information processing device, for example. By having the CPU 10 execute the program that is installed or stored in advance as described above, the information processing device as illustrated in FIG. 1 may function as the analysis device 1 of the present embodiment.

The memory device 18 may be a RAM (Random Access Memory) or an EEPROM (Electrically Erasable and Programmable Read Only Memory), for example. The interface device 20 controls connection with a network, for example. The input device 22 may include a keyboard, a mouse, a touch pad, a touch panel, and a microphone, for example. The display device 24 may be a display such as a LCD (Liquid Crystal Display) or a CRT (Cathode Ray Tube), for example.

Figure 2:
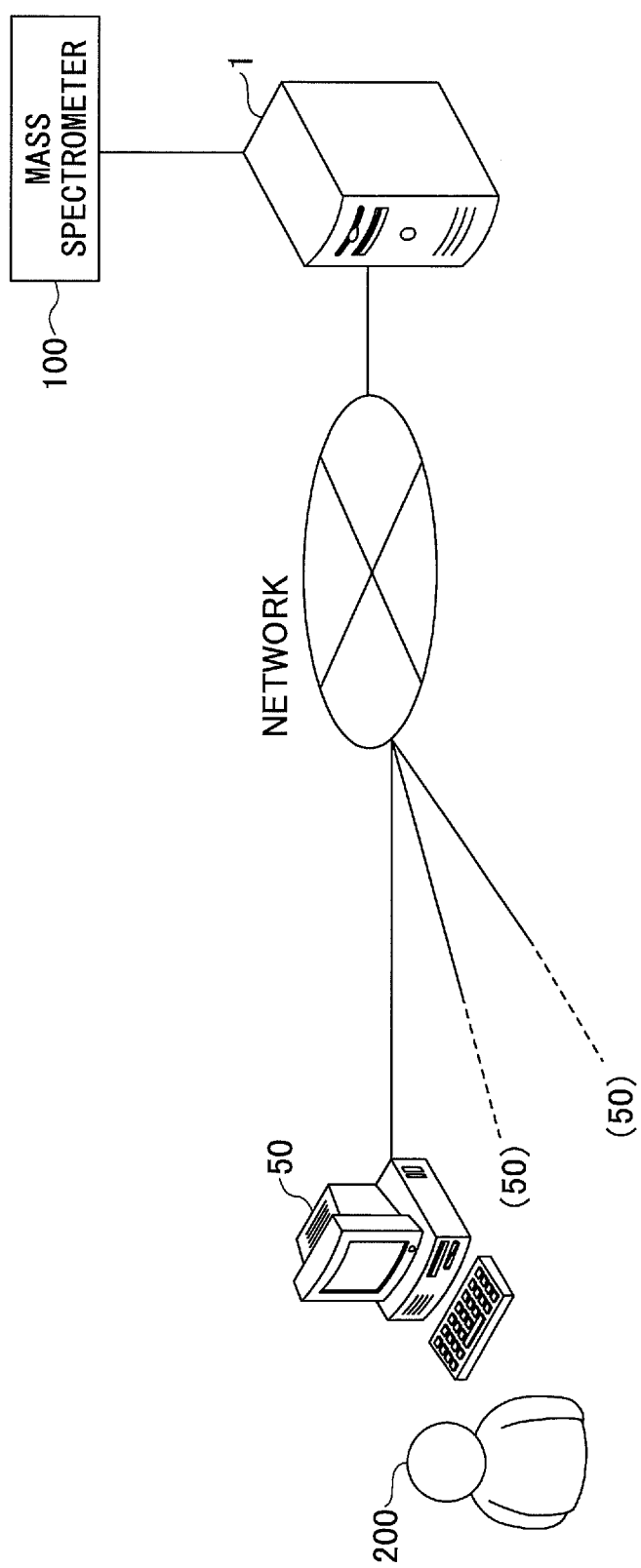
FIG. 2 illustrates another exemplary system configuration of the analysis device according to an embodiment of the present invention.

FIG. 2 illustrates another exemplary system configuration of the analysis device 1 according to the present embodiment. As illustrated in FIG. 2, the analysis device 1 may be implemented by a server device that is connected to one or more client computers 50 via a network. The client computer 50 may be operated by the user 200 to enter settings and commands, for example.

Figure 3:
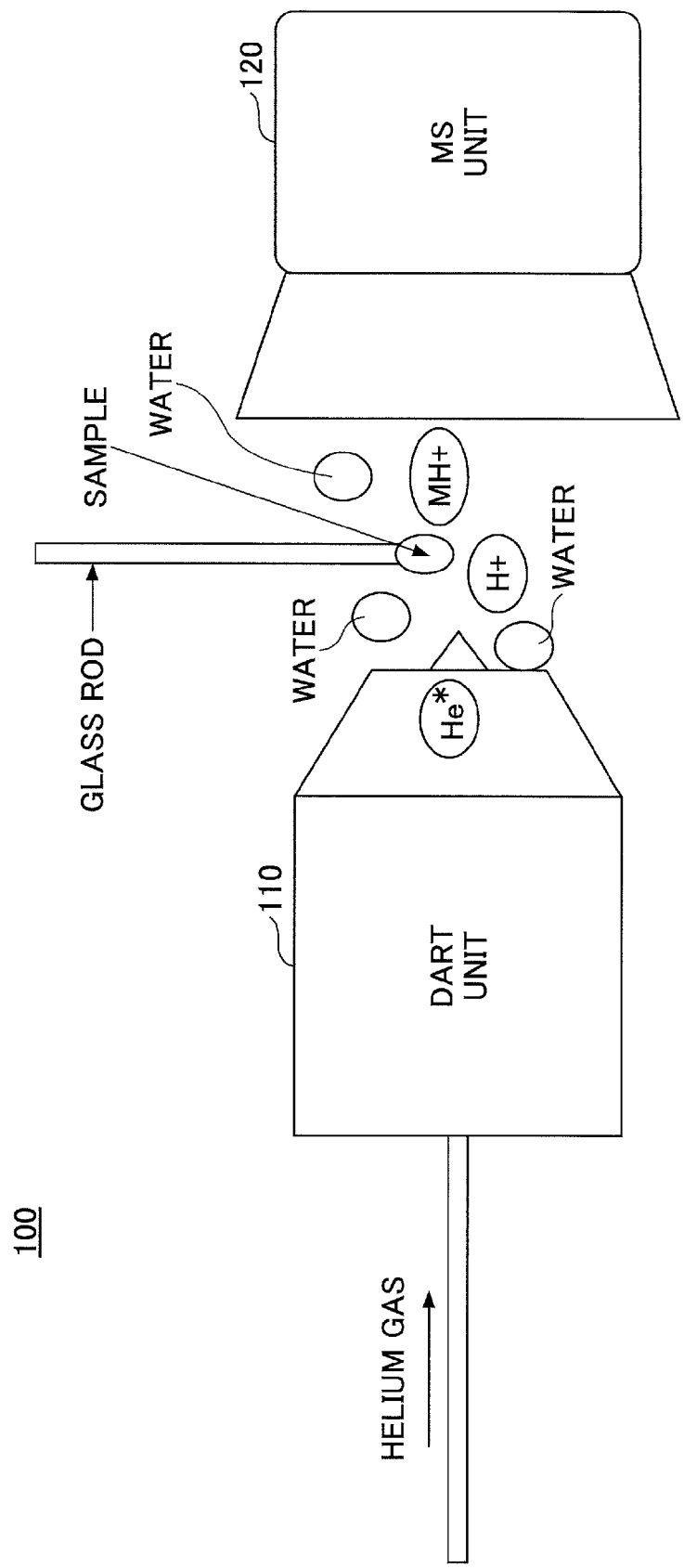
FIG. 3 schematically illustrates a configuration and a detection principle of a DART-MS.

The mass spectrometer 100 may be a DART-MS, for example. FIG. 3 schematically illustrates a configuration and a detection principle of the mass spectrometer 100 embodying a DART-MS. As illustrated in FIG. 3, the mass spectrometer 100 includes a DART unit 110 and a MS unit 120. The DART unit 110 may be implemented by a DART ion source such as DART SVS by IonSense, Inc., for example. The MS unit 120 may be implemented by a TOF-MS (Time of Flight Mass Spectrometer) such as micrOTOF-Q II by Bruker Daltonics, Inc., for example.

The DART unit 110 ionizes components on the surface of a sample substance by generating an electrical discharge from a needle electrode and causing excitation of gas such as He gas. The ionization process by the DART unit 110 is believed to occur in the following manner. He gas excited by glow discharge interacts with water molecules in the air to generate water cluster ions. The water cluster ions then prompt proton transfer reactions at the sample substance. The following equations (1)-(4) represent the proton transfer reactions occurring at the DART unit 110.

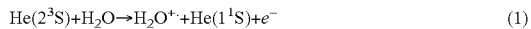

$$He(2^3S) + H_2O \rightarrow H_2O^{+\cdot} + He(1^1S) + e^- \quad (1)$$

$$H_2O^{+\cdot} + H_2O \rightarrow H_3O^+ + OH^{\cdot} \quad (2)$$

$$H_3O^+ + nH_2O \rightarrow [(H_2O)_nH]^+ \quad (3)$$

$$[(H_2O)_nH]^+ + M \rightarrow [M+H]^+ + nH_2O \quad (4)$$

The MS unit 120 detects the ionized sample substance and acquires a mass spectrum of the sample substance. The mass spectrum corresponds to two-dimensional data with one axis representing an intensity (ion count) distribution and the other axis representing the mass-to-charge ratio (m/z). Note that the mass spectrum may also be three-dimensional data including an additional axis representing time. However, it is assumed in the following descriptions that the mass spectrum corresponds to two-dimensional data. In the case where the mass spectrum corresponds to three-dimensional data, either the mass spectrometer 100 or the analysis device 1 may apply time integration to convert the three-dimensional data into two-dimensional data.

Note that the mass spectrometer 100 is not limited to the DART-MS as described above, but may also use other MS modes.

[Functional Configuration of Analysis Device]

Figure 4:
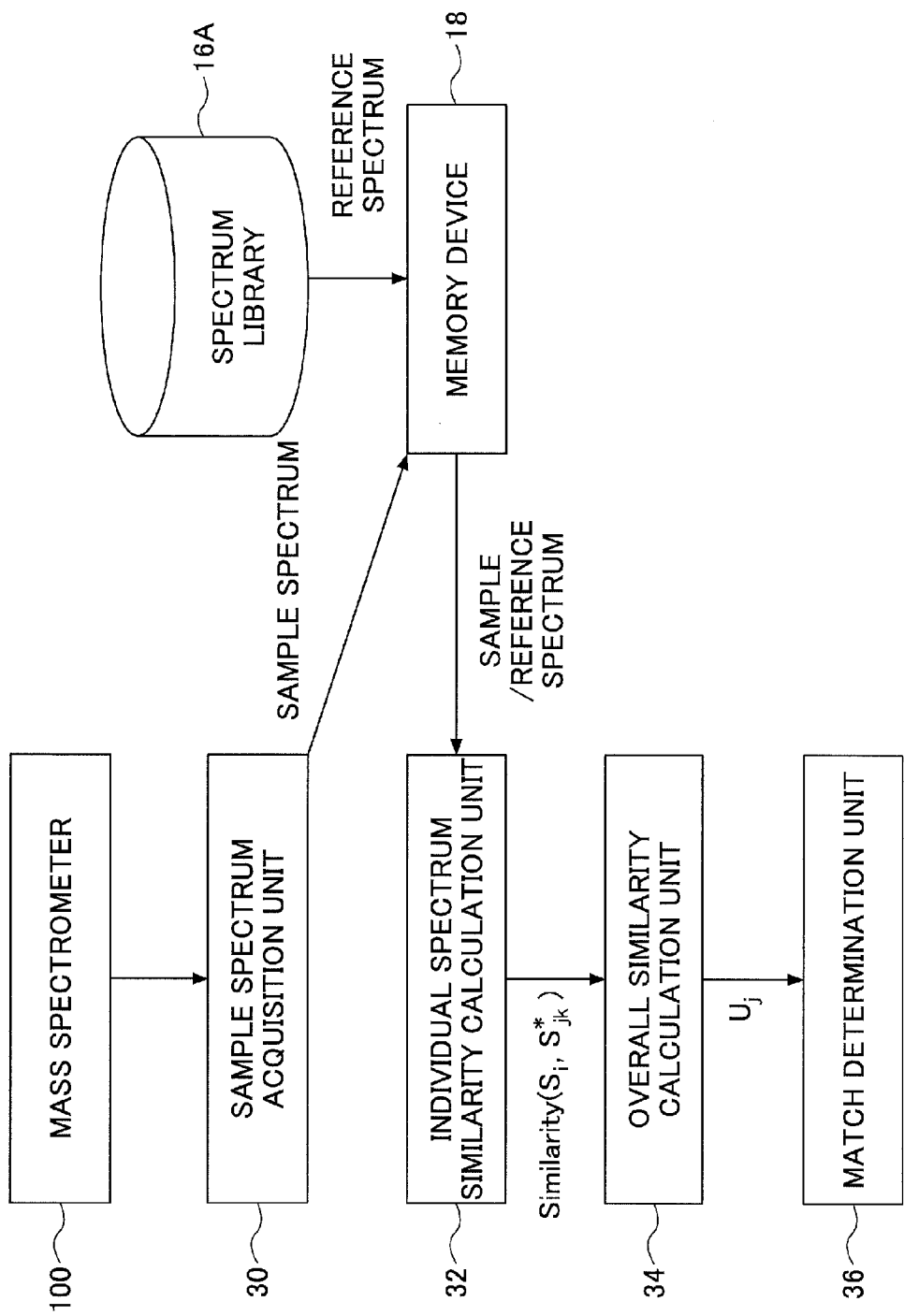
FIG. 4 illustrates an exemplary functional configuration of the analysis device according to a first embodiment.

FIG. 4 illustrates an exemplary functional configuration of the analysis device 1 according to the first embodiment. The analysis device 1 includes a sample spectrum acquisition unit 30, an individual spectrum similarity calculation unit 32, an overall similarity calculation unit 34, and a match determination unit 36.

The functional components of FIG. 4 may be implemented by the CPU 10 executing program software stored in the auxiliary storage device 16, for example. Note that the functional components do not necessarily have to be implemented by separate programs. For example, one of the functional components may be called by another functional component as a subroutine. Also, the functional components are not limited to implementation by software and may alternatively be implemented by hardware such as an IC (integrated circuit) or a FPGA (field programmable gate array), for example.

The sample spectrum acquisition unit 30 acquires, from the mass spectrometer 100 via the interface device 20, for example, a plurality of sample spectra $S_i$ obtained a plurality of times for the same sample substance, and stores the acquired sample spectra $S_i$ in the memory device 18. Note that the sample spectra $S_i$ already acquired from the mass spectrometer 100 may be stored in the auxiliary storage device 16, and the stored data may be retrieved and loaded in the memory device 18, for example.

The plurality of sample spectra $S_i$ correspond to time series data acquired from the mass spectrometer 100 a plurality of times over a course of time during which environmental conditions such as the temperature and the pressure are changed, for example. The index "i" (i=1~n) of the sample spectrum $S_i$ represents the sequential order of the spectrum data; namely, the number of times the spectrum data has been acquired. Specifically, the mass spectrometer 100 may be controlled to obtain a plurality of mass spectra over a course of time while the temperature within the mass spectrometer 100 is gradually raised, and the sample spectrum acquisition unit 30 may acquire the plurality of sample spectra $S_i$ from the mass spectrometer 100, for example.

The auxiliary storage device 16 stores a spectrum library 16A having a plurality of reference spectra $S^*_{jk}$ of a known substance j registered therein. The plurality of reference spectra $S^*_{jk}$ are compared with the sample spectra $S_i$. Like the sample spectra $S_i$, the plurality of reference spectra $S^*_{jk}$ correspond to time series data acquired a plurality of times over a course of time during which environmental conditions such as the temperature and the pressure are changed.

The index "j" of the reference spectra $S^*_{jk}$ corresponds to identification data of the known substance. The index "k" (k=1~n*) of the reference spectra $S^*_{jk}$ represents the sequential order of the spectrum data; namely, the number of times the spectrum data has been acquired. Note that the number "n" and "n*" do not necessarily have to be the same.

Figure 5:
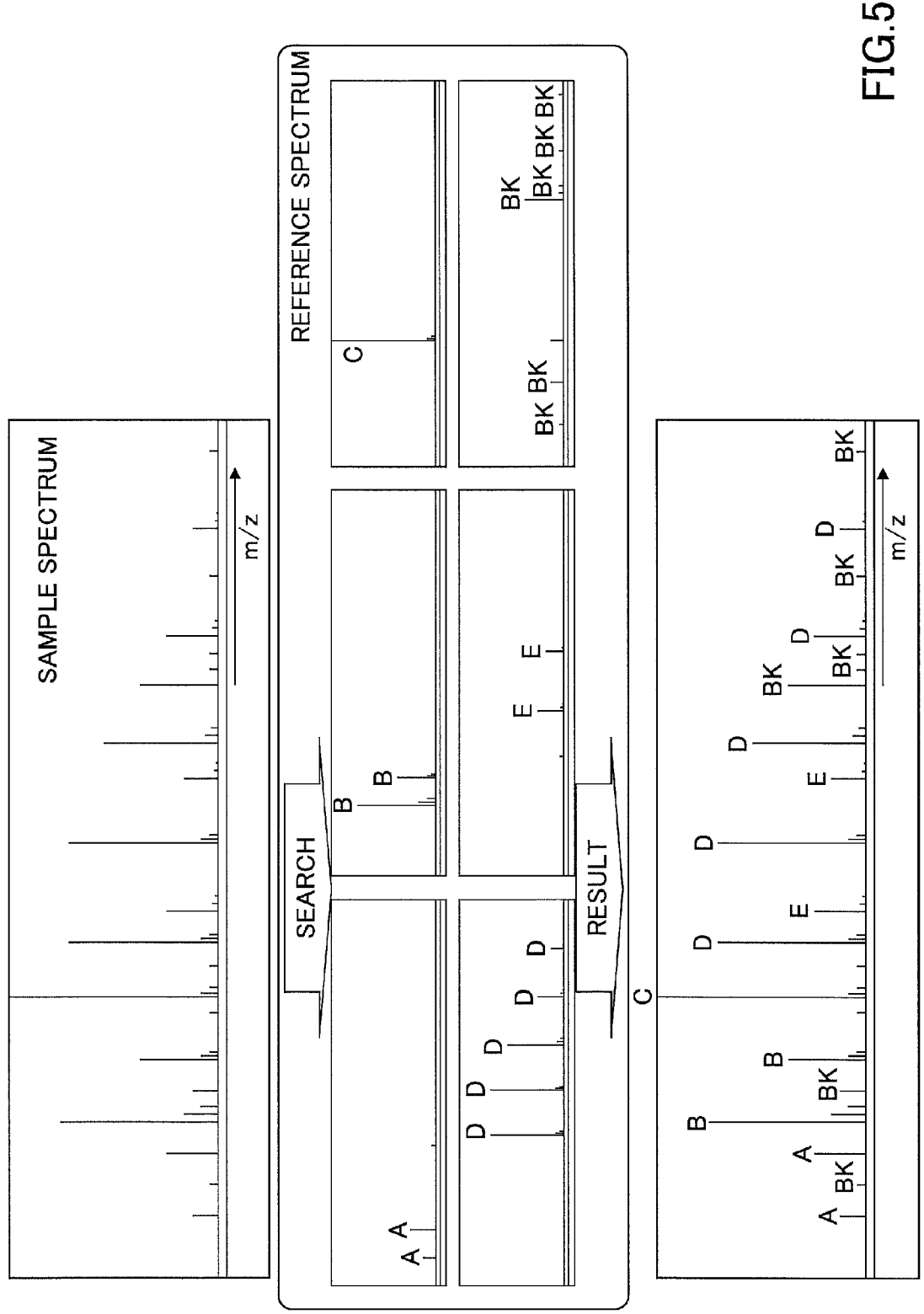
FIG. 5 illustrates how a plurality of reference spectra may be included in a sample spectrum.

The sample substance may be a single substance or a mixed substance. Similarly, the known substance may be a single substance or a mixed substance. However, the known substance is preferably a simpler compound compared to the sample substance. That is, the sample spectra $S_i$ may be composite data of a plurality of mass spectra, and the reference spectra $S^*_{jk}$ may be simpler data that may be included in the sample spectra $S_i$. FIG. 5 illustrates how a plurality of reference spectra may be included in a sample spectrum. As illustrated, when a sample spectrum $S_i$ includes a portion partially overlapping with a reference spectrum $S^*_{jk}$, it is determined that the sample spectrum $S_i$ includes the reference spectrum $S^*_{jk}$. In FIG. 5, the horizontal axis represents the mass-to-charge ratio (m/z) and the vertical axis represents the intensity. Also, in FIG. 5, A-E represent reference spectra $S^*_{jk}$ of known substances and BK represents the background (steady-state error resulting from mass spectrometry characteristics and the measurement environment, for example).

Figure 6:
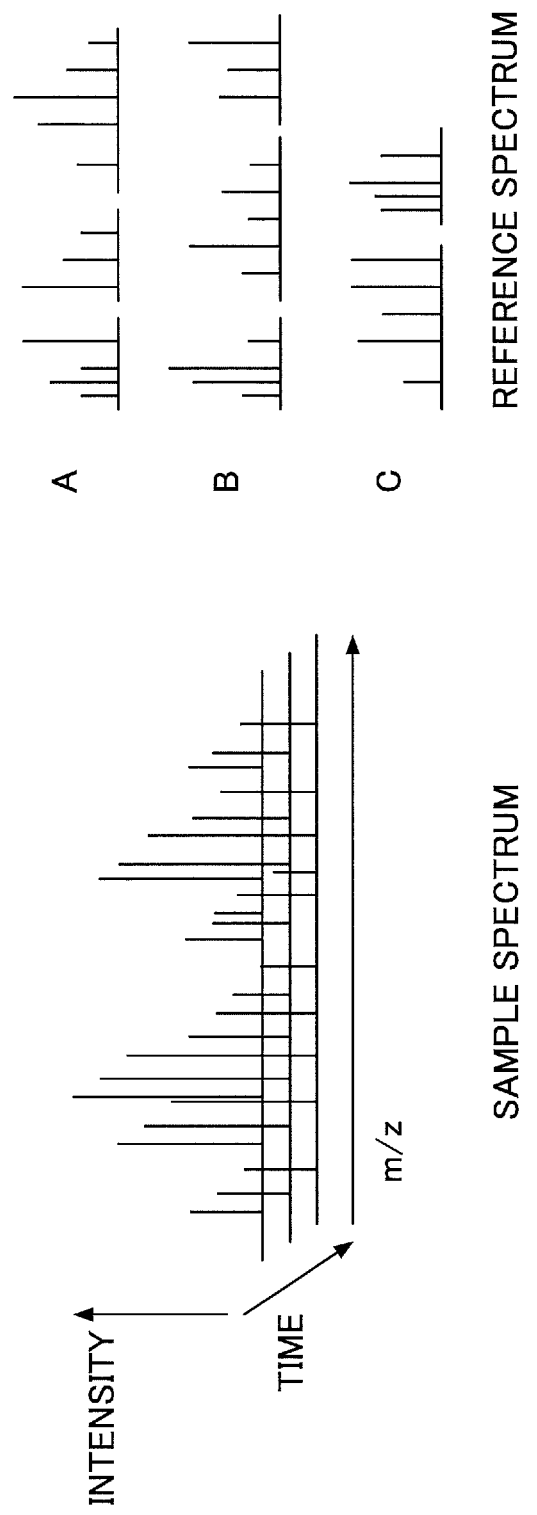
FIG. 6 illustrates reference spectra and sample spectra reflecting time components.

FIG. 6 illustrates reference spectra and sample spectra reflecting time components.

Figures 7, 8:
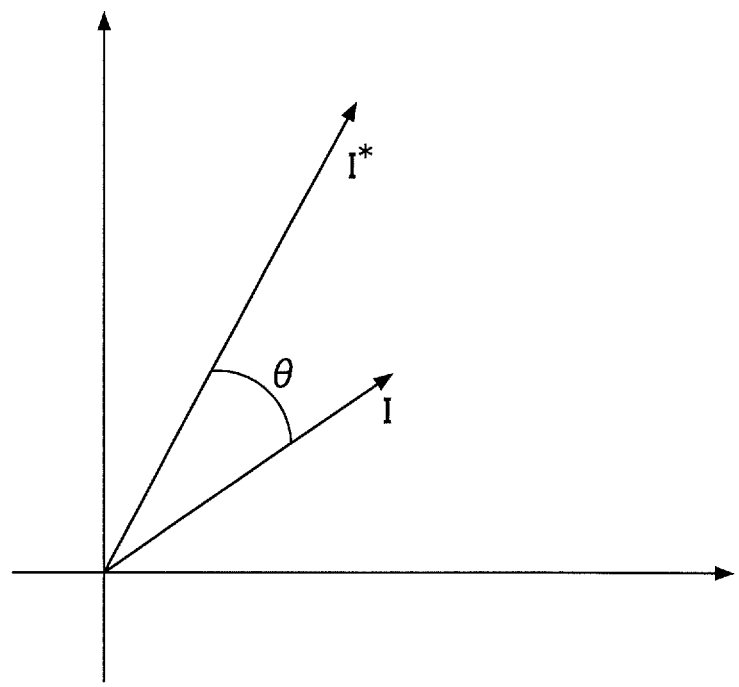
FIG. 7 illustrates an example of vector data.
FIG. 8 schematically illustrates an angle formed by two sets of vector data on a two-dimensional plane.

In the present embodiment, the reference spectra $S^*_{jk}$ correspond to vector data I* with a step size of about 1 m/z set up as the data label and having intensity data assigned only to a m/z forming a peak (i.e., intensity data is not assigned to a m/z that does not correspond to a peak). FIG. 7 illustrates an example of vector data I*.

[Individual Spectrum Similarity: Between Plurality of Spectra Acquired]

The individual spectrum similarity calculation unit 32 performs the following process steps under the assumption that the sample substance is a mixture of a plurality of known substances.

First, the individual spectrum similarity calculation unit 32 performs a process of removing noise from the plurality of sample spectra $S_i$. As the noise removal process, for example, the individual spectrum similarity calculation unit 32 may correct a value that falls below a recursive threshold value to zero, the recursive threshold value being obtained based on the intensity distribution of the plurality of sample spectra $S_i$. For example, the individual spectrum similarity calculation unit 32 may divide a m/z range of a sample spectrum into a plurality of segments, remove a high intensity value corresponding to a peak within the segments, determine the threshold value based on the average value of the remaining intensity values, and correct an intensity value falling below the threshold value to zero (0).

Then, the individual spectrum similarity calculation unit 32 extracts one set of data from each of the plurality of sample spectra $S_i$ and the plurality of reference spectra $S^*_{jk}$, compares a peak intensity ratio of the extracted reference spectrum $S^*_{jk}$ and a peak intensity of a portion of the extracted sample spectrum $S_i$ corresponding to the peak in the extracted reference spectrum $S^*_{jk}$, and calculates an individual spectrum similarity $(S_i, S^*_{jk})$ representing a similarity between the sample spectrum $S_i$ and the reference spectrum $S^*_{jk}$. Note that the individual spectrum similarity $(S_i, S^*_{jk})$ is basically calculated for all combinations of the sample spectrum and the reference spectrum (i.e., i×j×k different combinations) in the present embodiment; however some form of refinement or branch and bound method may be applied instead of mechanically obtaining the similarity for all combinations.

The individual spectrum similarity calculation unit 32 may extract an intensity of the sample spectrum $S_i$ at the m/z equal to the m/z forming a peak in the reference spectrum $S^*_{jk}$ (m/z set up as the data label of the above reference spectrum $S^*_{jk}$) or a maximum intensity of the sample spectrum $S_i$ at a m/z within a certain tolerance range of the m/z forming a peak at the reference spectrum $S^*_{jk}$, and generate vector data I of the same degree as the vector data I* of the reference spectrum $S^*_{jk}$.

Figure 19:
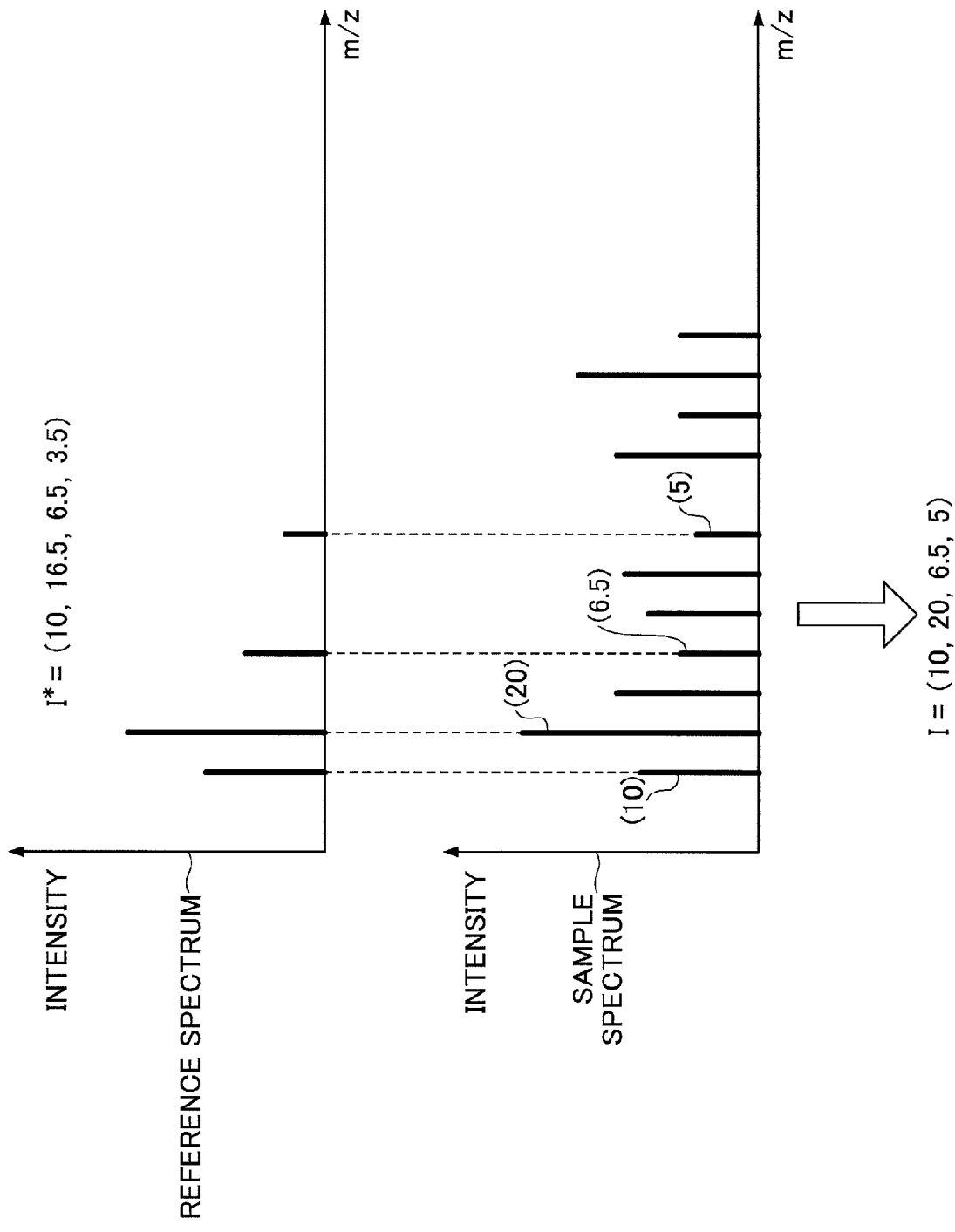
FIG. 19 illustrates how vector data of the same degree as vector data of a reference spectrum is generated by extracting an intensity of a sample spectrum at a m/z equal to or within a certain tolerance range of a m/z forming a peak in the reference spectrum.

FIG. 19 illustrates how the vector data I of the same degree as the vector data I* of the reference spectrum $S^*_{jk}$ may be generated by extracting the intensity of the sample spectrum $S_i$ at the m/z equal to or within a certain tolerance range of the m/z forming a peak in the reference spectrum $S^*_{jk}$. In a case where the sample spectrum $S_i$ does not have a peak at the m/z equal to or within a certain tolerance range of the m/z forming a peak in the reference spectrum $S^*_{jk}$, the individual spectrum similarity calculation unit 32 sets the corresponding component of the vector data I to zero (0). In FIG. 19, the intensities at the m/z forming peaks in the sample spectrum $S_i$ are (10, 20, 12.5, 6.5, 9.5, 11, 5, 12.5, 6.5, 14, 6.5). Of the above peak intensities, the intensities at the m/z equal to or within a certain tolerance range of the m/z forming peaks in the reference spectrum $S^*_{jk}$ are extracted, and as a result, I=(10, 20, 6.5, 5) is obtained.

Then, the individual spectrum similarity calculation unit 32 calculates the individual spectrum similarity ($S_i$, $S^*_{jk}$) for each combination of the sample spectrum $S_i$ and the reference spectrum $S^*_{jk}$ based on the following equation (5). Note that in equation (5), $I_m$ represents the $m^{th}$ component of the vector data I, and $I^*_m$ represents the $m^{th}$ component of the vector data I*.

$$Similarity_a(S_i, S^*_{jk}) = \frac{(I, I^*)}{\|I\| \cdot \|I^*\|} = \frac{\sum (I_m \cdot I^*_m)}{\sqrt{\sum I_m^2} \cdot \sqrt{\sum I_m^{*2}}} \quad (5)$$

As can be appreciated from the above equation (5), assuming θ represents an angle formed by the vector data I and the vector data I*, the individual spectrum similarity ($S_i$, $S^*_{jk}$) corresponds to cos θ. FIG. 8 schematically illustrates the relationship between the angle θ and the vector data I and I* on a two-dimensional plane.

Note that the method of calculating the individual spectrum similarity ($S_i$, $S^*_{jk}$) is not limited to the above method. For example, the Pearson product-moment correlation coefficient may be used to obtain the individual spectrum similarity ($S_i$, $S^*_{jk}$). The following equation (6) represents a computing equation in a case where the Pearson product-moment correlation coefficient is used to obtain the individual spectrum similarity ($S_i$, $S^*_{jk}$). In another example, as illustrated by the following equation (7), the individual spectrum similarity ($S_i$, $S^*_{jk}$) may be obtained by multiplying the equation (5) or the equation (6) by an ion count ratio (value obtained by dividing a total value of the components of the vector data I by a total ion count $I_{total}$; i.e., a total value of the intensities for all m/z values).

$$Similarity_b(S_i, S^*_{jk}) = \frac{\sum (I_m - \bar{I}) \cdot \sum (I^*_m - \bar{I^*})}{\sqrt{\sum (I_m - \bar{I})^2} \cdot \sqrt{\sum (I^*_m - \bar{I^*})^2}} \quad (6)$$

$$Similarity_c(S_i, S^*_{jk}) = \frac{\sum I_m}{I_{total}} \cdot \frac{\sum (I_m \cdot I^*_m)}{\sqrt{\sum I_m^2} \cdot \sqrt{\sum I_m^{*2}}} \quad (7)$$

[Overall Similarity: Between Sample Substance and Known Substance]

The overall similarity calculation unit 34 calculates an overall similarity $U_j$=Similarity (S, $S^*_j$) representing a similarity between the sample substance and the known substance j based on the individual spectrum similarity ($S_i$, $S^*_{jk}$) calculated by the individual spectrum similarity calculation unit 32.

FIG. 9 illustrates matrix data representing a plurality of individual spectrum similarities ($S_i$, $S^*_{jk}$) calculated by the individual spectrum similarity calculation unit 32 for the known substance j. Based on such matrix data, the overall similarity calculation unit 34 selects one set of data (i.e., selects a combination of a sample spectrum $S_i$ and a reference spectrum $S^*_{jk}$) from each line k=1~n* and divides a total value of the selected data by n* to calculate the overall similarity $U_j$.

(1) In the above data selection, a rule is implemented such that when data at the $i^{th}$ row is selected from line k, data at or above the $(i-1)^{th}$ row may not be selected from line k+1. That is, the rule calls for obtaining the shortest path from the upper left side of the matrix data to the lower right side of the matrix data (no moving back up or to the left). Such a rule is imposed to prevent the data selection from being inconsistent with the sequential order of the sample spectra $S_i$ and the reference spectra $S^*_{jk}$.

(2) Also, the data selection is performed such that the total value of the individual spectrum similarities ($S_i$, $S^*_{jk}$) of the selected path equals a maximum value.

A most reliable process for satisfying the above conditions (1) and (2) involves obtaining the total value of individual spectrum similarities ($S_i$, $S^*_{jk}$) for all paths satisfying the above condition (1) and selecting the data representing the maximum value. The above-described process may be used, or alternatively, an algorithm for obtaining an approximate solution may be used as described below.

The following equation (8) is an equation for obtaining a partial total value $W_{i,k}$. Note that in equation (8), $V_{i,k}$ corresponds to an abbreviated representation of the individual spectrum similarity ($S_i$, $S^*_{jk}$).

$$W_{i,k} = \max \begin{cases} W_{i-1,k} \\ W_{i-1,k-1} + V_{i,k} \\ W_{i,k-1} + V_{i,k} \end{cases} \quad (8)$$

The partial total value $W_{i,k}$ is sequentially obtained from the upper left side of the matrix data. In the following, a specific example of obtaining such a value based on the data illustrated in FIG. 9 is described. With respect to $W_{1,1}$, because data corresponding to $W_{1-1,1}$, $W_{1-1,1-1}$, and $W_{1,1-1}$ do not exist, their corresponding values are set equal to zero (0), and as a result, $W_{1,1}=V_{1,1}=0.5$ is obtained. With respect to $W_{1,2}$, although $W_{1-1,2}$ and $W_{1-1,2-1}$ are equal to zero (0), $W_{1,2-1}$ is equal to 0.5. Thus, the third item of equation (8) is used to obtain 0.5+0.2=0.7. With respect to $W_{2,1}$, $W_{2-1,1}$ is equal to 0.5, whereas $W_{2-1,1-1}$ and $W_{2,1-1}$ are equal to zero (0). Thus, the first item of equation (8) is used to obtain 0.5. In this way, a process of sequentially obtaining the partial total value $W_{i,k}$ may be performed. FIG. 10 illustrates partial total values $W_{i,k}$ calculated for the matrix data of FIG. 9. In FIG. 10, an arrow indicates a reference used in equation (8), and an underlined block represents the selected combination of the sample spectrum $S_i$ and the reference spectrum $S^*_{jk}$. Note that the corresponding reference spectrum $S^*_{jk}$ of such a block may be referred to as "matching spectrum".

Then, with respect to each line, data at the uppermost row of the data representing the maximum value of the partial total values $W_{i,k}$ is determined to be the selected data, and the overall similarity $U_j$ is obtained by dividing the partial total value $W_{n,n^*}$ at the lower right side by $n^*$ (see equation (9) below). In the example of FIG. 10, $U_j=3.2/5=0.64$.

$$U_j = W_{n,n^*}/n^* \qquad (9)$$

By using the above-described algorithm, at least the rule imposed by condition (1) may be satisfied and an approximate solution satisfying condition (2) at a high probability may be obtained. Note that in the case of obtaining the total value of individual spectrum similarities ($S_i$, $S^*_{jk}$) for all paths satisfying the above condition (1) and selecting the data representing the maximum value as described above, the calculation time is in the order of $2^{n+n'}$. On the other hand, in the case of using the algorithm for obtaining an approximate solution as described above, the calculation time may be reduced to an order of $n \cdot n^*$.

After the overall similarity calculation unit 34 calculates the overall similarity $U_j$, if the overall similarity $U_j$ is greater than a threshold value, for example, a determination result indicating that the sample substance includes the known substance j may be output to the display device 24 (by the match determination unit 36 as described below), or the overall similarity $U_j$ may be output to the display device 24, for example.

In this way, a user may obtain accurate information concerning whether the sample substance includes the known substance j and may use such information in identifying the sample substance.

Also, in a preferred embodiment, in addition to presenting the calculated overall similarity $U_j$, a list of "matching spectra" corresponding to the reference spectra $S^*_{jk}$ that have been determined to "match" the sample spectra $S_i$ may be presented. In this way, data may be retrieved relating to "the timing at which a mass spectrum was obtained; i.e., the environment under which the mass spectrum was obtained, and the reference spectrum that resembles the mass spectrum" (e.g., what kind of mass spectrum was obtained after how many minutes from the start of testing and at what temperature). Thus, the user may obtain even more accurate information concerning whether the sample includes the know substance j.

In the case where the above-described algorithm is used to calculate the overall similarity $U_j$, extraction of the matching spectra may be performed by a trace back process as described below. Note that in this case, the arrows shown in FIG. 10 indicate a trace back path, and the underlined blocks indicate the matching spectra.

1. Start from $W_{n,n'}$.
2. If $W_{i-1,k}$ is the same as $W_{i,k}$, move to $W_{i-1,k}$.
3. If $W_{i-1,k}$ is less than $W_{i,k}$, move to the greater one of $W_{i-1,k}$ or $W_{i-1,k-1}$. In this case, the reference spectrum $S^*_{jk}$ corresponding to $W_{i,k}$ is the matching spectrum.
4. Repeat steps 2 and 3 until reaching $W_{i-1}$.

[Match Determination]

Figure 11:
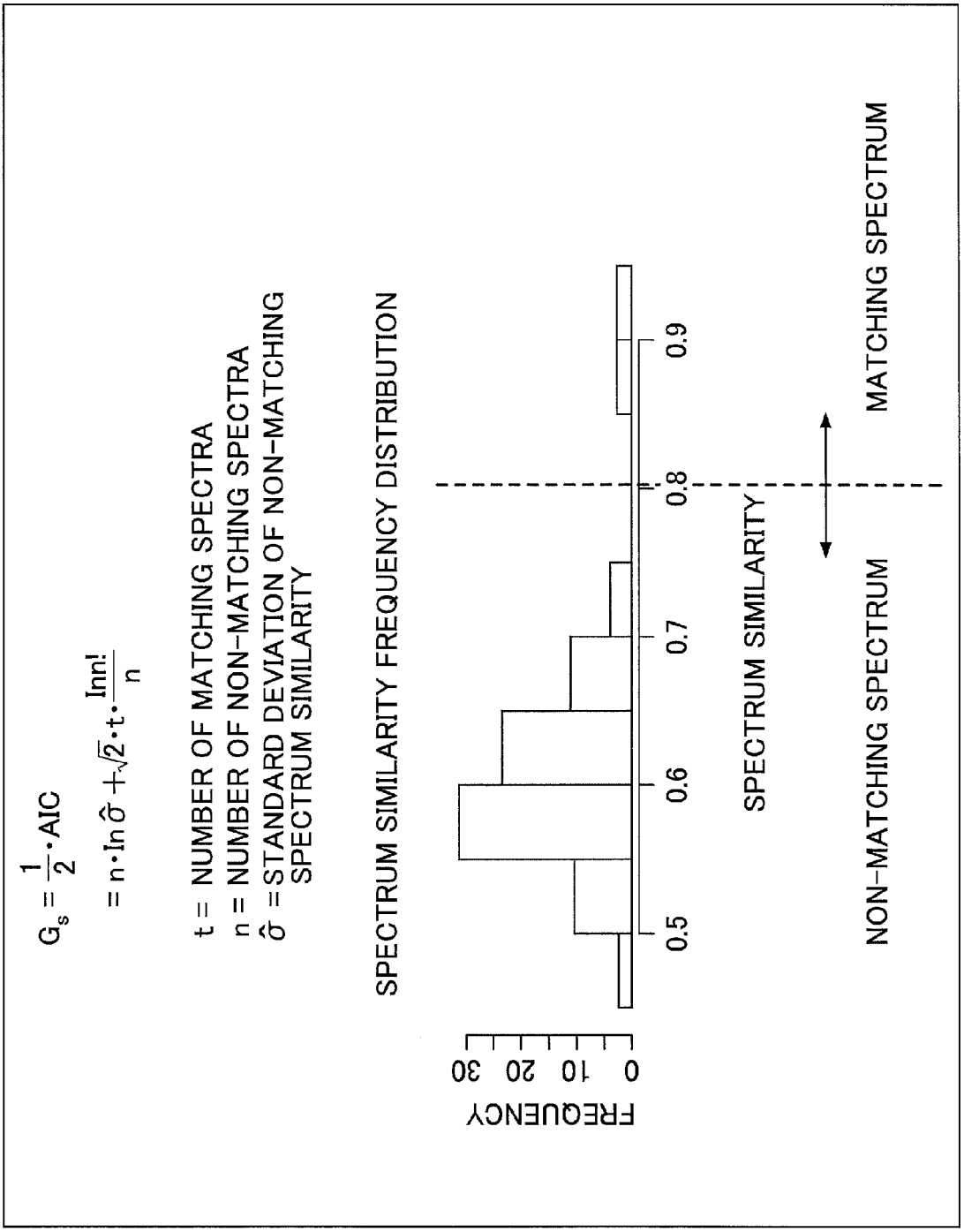
FIG. 11 schematically illustrates a principle for identifying a matching substance and a non-matching substance using a statistical model.

In a case where the number of reference spectra $S^*_{jk}$ registered in the spectrum library 16A is relatively small, the match determination unit 36 may perform a determination process by simply using a threshold value as described above. Alternatively, in a preferred embodiment, a determination process may be recursively performed using a statistical model. For example, under the assumption that "the overall similarity $U_j$ for a known substance j that does not match the sample substance (non-matching substance) represents a normal distribution because the non-matching substance constitutes a majority," the known substance matching the sample substance (matching substance) may be determined by calculating the Akaike's Information Criterion (AIC) of a normal distribution of the overall similarity $U_j$ excluding those of known substances with a high overall similarity $U_j$ and determining the value t of $G_t$ having the minimum AIC value. FIG. 11 schematically illustrates a principle for determining a matching substance and a non-matching substance using a statistical model. Also, a determination process may be performed using other statistical models such as the Smirnov-Grubbs test. The Smirnov-Grubbs test involves detecting a high value deviating from the normal distribution as an outlier (in the present example, non-matching substance=hit).

By recursively making a determination as to whether a sample includes a known substance j based on the distribution of the overall similarity $U_j$ as described above, the user may obtain more accurate information concerning whether the sample includes the known substance j.

[Process Flow]

Figure 12A:
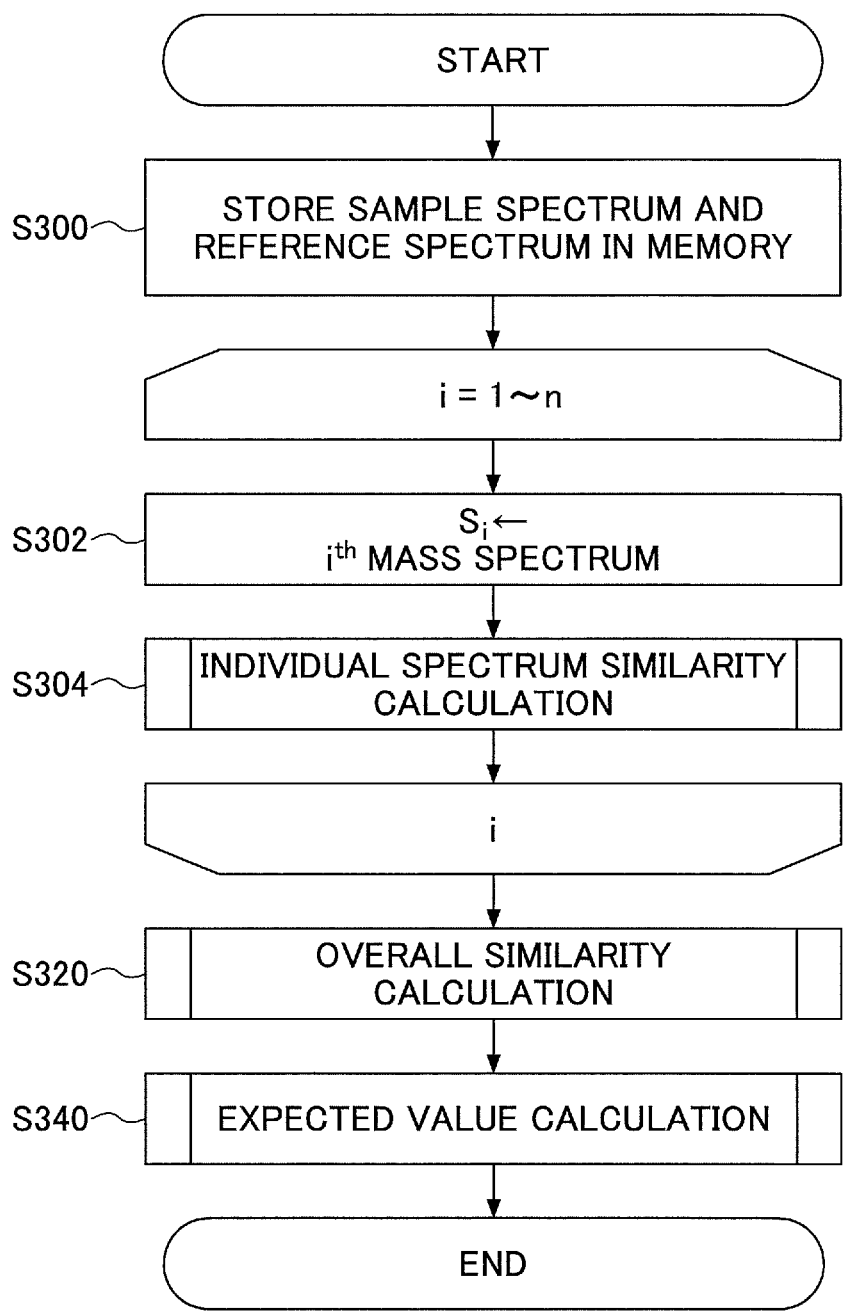
FIG. 12A is a flowchart illustrating a process flow of the analysis device of the first embodiment.

FIG. 12A is a flowchart illustrating a process flow of the analysis device 1 of the first embodiment. The illustrated process flow is implemented through cooperation of the various functional blocks of the analysis device 1.

First, the plurality of sample spectra $S_i$ are stored in the memory device 18, and likewise, the plurality of reference spectra $S^*_{jk}$ are stored in the memory device 18 (step S300). Note that the above spectra data do not necessarily have to be loaded in the memory device 18, but instead, the spectra data stored in the auxiliary storage device 16 may be used, for example.

Figure 12B:
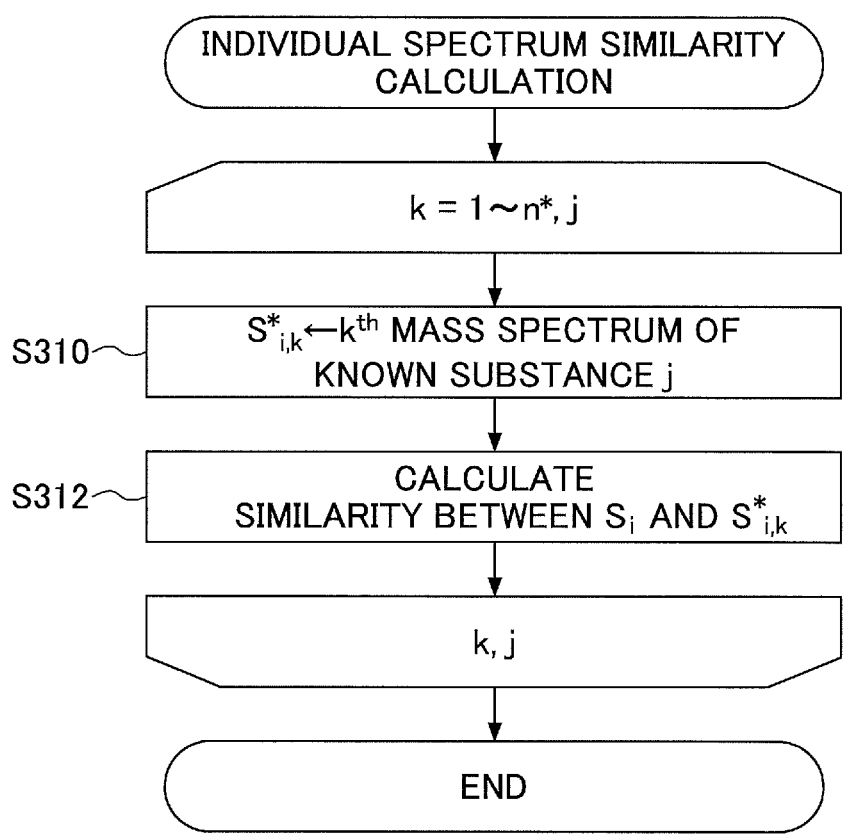
FIG. 12B is a flowchart illustrating a process flow for individual spectrum similarity calculation.

Next, process steps S302 and S304 are performed with respect to each of the plurality of sample spectra $S_i$ (i=1~n). In step S302, the $i^{th}$ mass spectrum is extracted as sample spectrum $S_i$ from the plurality of sample spectra. In step S304, individual spectrum similarity calculation is performed with respect to the extracted sample spectrum $S_i$. FIG. 12B is a flowchart illustrating a process flow of the individual spectrum similarity calculation.

In the individual spectrum calculation, process steps S310 and S312 are performed with respect to each of the plurality of reference spectra $S^*_{jk}$ (where j represents a number of a known substance, and k=1~n*). In step S310, the $k^{th}$ mass spectrum of the $j^{th}$ known substance is extracted as reference spectrum $S^*_{jk}$ from the plurality of reference spectra. Then, in step S312, a similarity between the sample spectrum $S_i$ and the reference spectrum $S^*_{jk}$ is calculated.

Figure 12C:
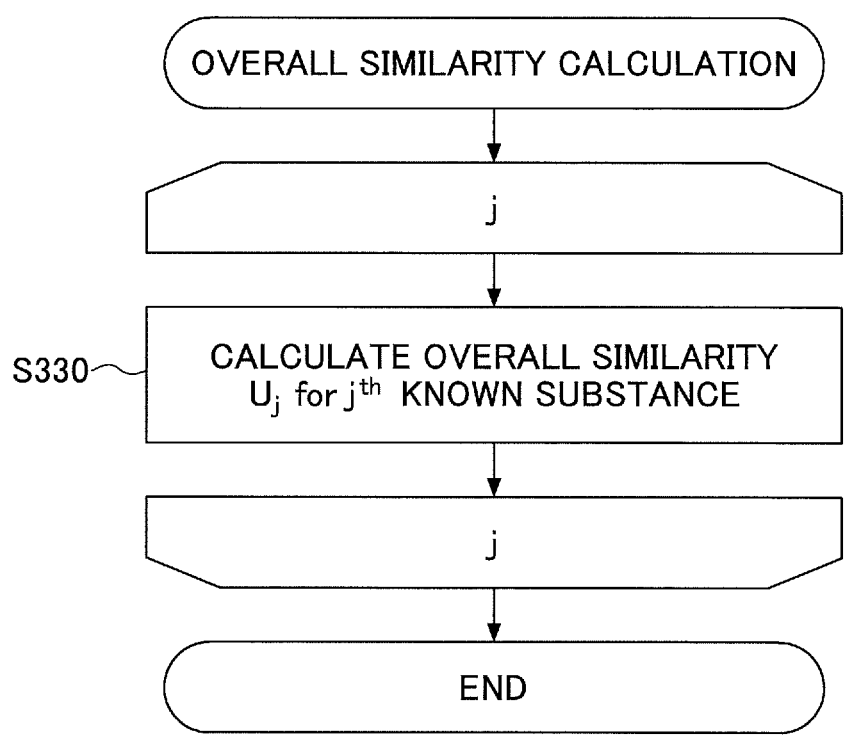
FIG. 12C is a flowchart illustrating a process flow for overall similarity calculation.

After the loop process of steps S302-S312 is completed, overall similarity calculation is performed in step S320. FIG. 12C is a flowchart illustrating a process flow of the overall similarity calculation.

In the overall similarity calculation, process step S330 is performed with respect to each of the known substances j. In steps S330, the overall similarity $U_j$ for the $j^{th}$ known substance is calculated.

Figure 13:
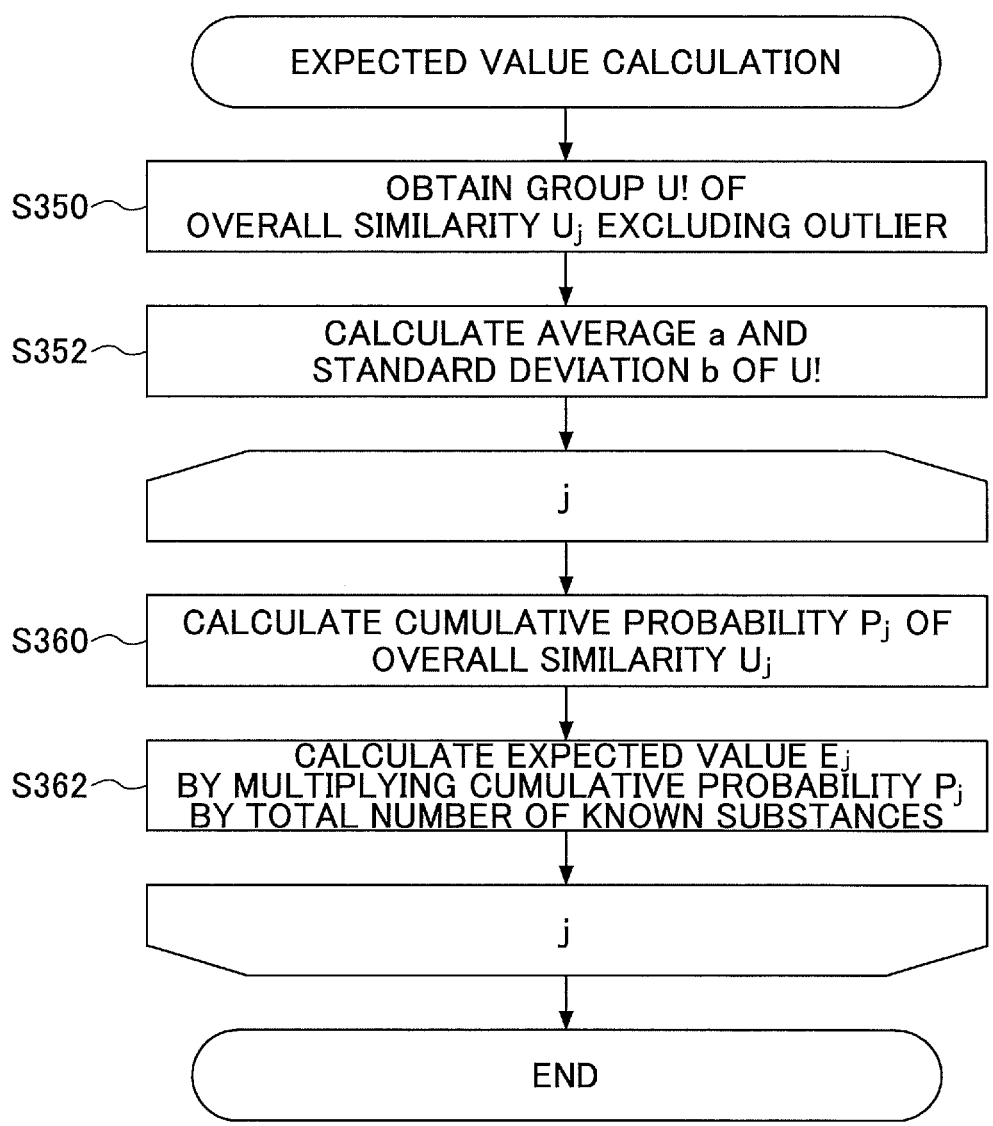
FIG. 13 is a flowchart illustrating a process flow for expected value calculation.

After the overall similarity $U_j$ is calculated for all the known substances j, expected value calculation is performed in step S340. FIG. 13 is a flowchart illustrating a process flow of the expected value calculation.

In the expected value calculation, a group U! of the overall similarities $U_j$ excluding outliers is obtained (step S350).

Then, an average value "a" and a standard deviation "b" of the group U! are calculated (step S352).

Figure 14:
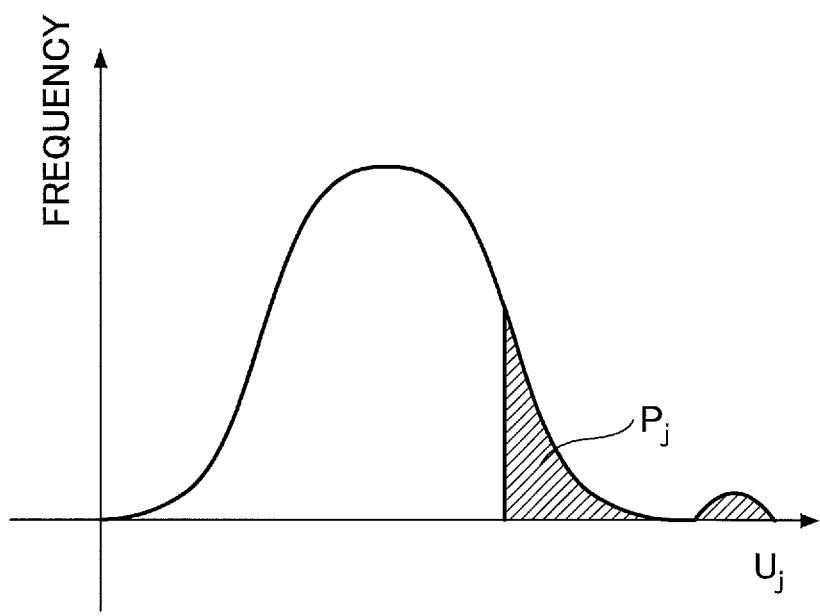
FIG. 14 is a graph illustrating a cumulative probability.

Then, process steps S360-S362 are performed with respect to each of the known substances j. In step S360, a cumulative probability $P_j$ of the overall similarity $U_j$ for a normal distribution defined by the average value "a" and the standard deviation "b" is calculated. FIG. 14 illustrates the cumulative probability $P_j$. As illustrated, the cumulative probability $P_j$ corresponds to a value obtained by integrating the frequency (occurrence number) from the side of overall similarity $U_j$ with a higher value.

Then, the cumulative probability $P_j$ is multiplied by the total number of known substances, and an expected value $E_j$ of the $j^{th}$ known substance is calculated (step S362). As can be appreciated from above, the expected value $E_j$ is an index value that indicates a higher matching probability with a sample substance as its value becomes smaller. After the expected value $E_j$ is calculated, a match determination process may be performed based on the expected value $E_j$ and the determination result may be output, or the expected value $E_j$ itself may be output in the form of a list, for example.

[Experiment]

The inventors of the present invention conducted experimentation and analysis of measurement data under the following conditions. First, the following ten types of specimen were prepared for registration as known substances in the spectrum library 16A: (1) Lidocain, (2) Diphenhydramine and hydrogenated polyoxy 60 castor oil (HCO60) mixture, (3) Tocopherol acetate, (4) EcoGum, (5) Polypropylene, (6) Urea, (7) Solanine, (8) Crotamiton, (9) Caffeine, (10) Irganox1010. Note that of the above known substances, (2) Diphenhydramine and HCO60 mixture is a mixture of two compounds.

As a sample substance, cream A that is known to contain three of the above known substances (i.e., (1), (2), and (3)) was used.

The above known substances and sample substance were then measured under the following device and measurement conditions. As the mass spectrometer 100, MicrOTOF-QII (by Bruker Corporation) having DART SVP (by IonScence, Inc.) installed therein was used. Also, as the measurement conditions, the measurement mode was set to positive ion mode (measurement range m/z: 150-500), the sample was measured by gradually raising the temperature from 30° C. to 400° C. over a time course of 10 minutes, and the known substances were measured at 500° C.

After the measurements were made by the mass spectrometer 100, the reference spectra $S^*_{jk}$ of the known substances were output as XML format files using MicrOTOF control (by Bruker Corporation). In this case, two (k=2) spectra corresponding to Diphenhydramine and HCO60 were selected for the known substance (2), and one (k=1) spectrum was selected for each of the other known substances. The sample spectra $S_i$ were converted to centroid mode mzML format files using CompassXport (by Bruker Corporation).

Then, processes according to the flowcharts of FIGS. 12A-12C and 13 were executed. In this case, the m/z tolerance between the reference spectrum $S^*_{jk}$ and the sample spectrum $S_i$ was set equal to 100 ppm. In calculating the individual spectrum similarity between the reference spectrum $S^*_{jk}$ and the sample spectrum $S_i$, the above composite value equation (7) was used. The overall similarity $U_j$ was calculated using the above algorithm for obtaining an approximate solution.

Then, a known substance with an expected value $E_j$ of less than 0.05 was determined to be a component of the sample.

FIG. 15 illustrates measurement results of the above experiment and analysis. In FIG. 15, "hit number" corresponds to a serial number assigned to the known substances according to their similarity with the sample substance, "substance identifier" corresponds to an ID identifying the known substance registered in the spectrum library 16A, "substance name" corresponds to the name of the known substance registered in the spectrum library 16A. Also, "spectrum number" corresponds to a serial number assigned to each spectrum of each known substance according to its sequential order.

In the present experiment, three types of known substances with expected values $E_j$ of less than 0.05 were detected. The known substances, in the order in which they were identified, correspond to the known substances (2), (1), and (3) registered in the spectrum library 16A. That is, all three types of known substances that were known components of the sample substance could be detected and identified in the present experiment.

[Summary]

As can be appreciated from the above descriptions, by using the analysis device 1 according to the present embodiment, a mass spectrum including a plurality of components may be analyzed and used in identifying a sample.

<Second Embodiment>

In the following, an analysis device 2 according to a second embodiment of the present invention is described with reference to the accompanying drawings.

[Basic Configuration]

The basic configuration of the analysis device 2 according to the second embodiment may be identical to that of the first embodiment so that descriptions thereof are omitted.

[Functional Configuration of Analysis Device]

Figure 16:
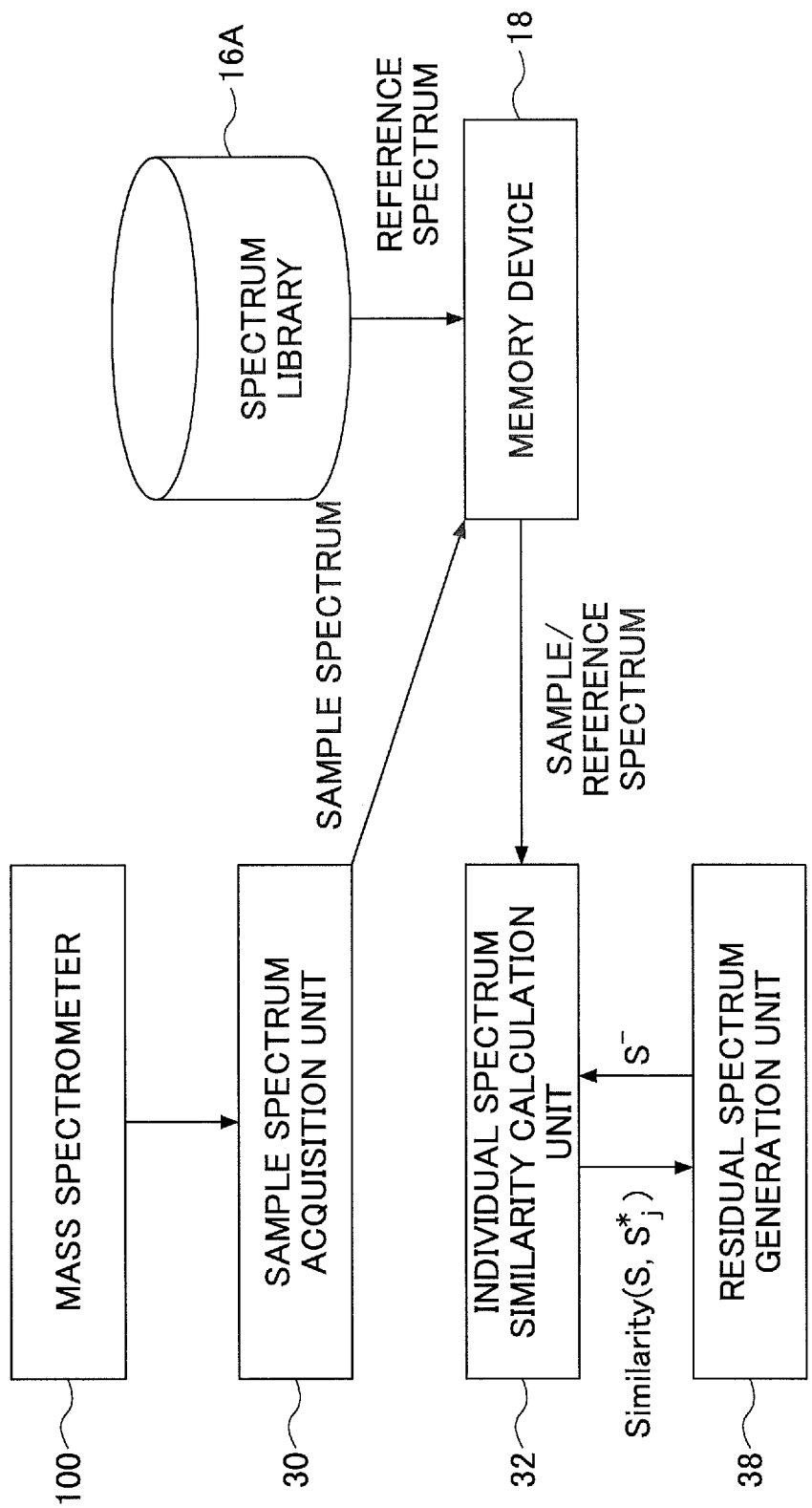
FIG. 16 illustrates an exemplary functional configuration of an analysis device according to a second embodiment of the present invention.

FIG. 16 illustrates a functional configuration of the analysis device 2 of the present embodiment. The analysis device 2 includes the sample spectrum acquisition unit 30, the individual spectrum similarity calculation unit 32, and a residual spectrum generation unit 38.

The above functional components may be implemented by the CPU 10 executing program software stored in the auxiliary storage device 16, for example. Note that the functional components do not necessarily have to be implemented by separate programs. For example, one of the functional components may be called by another functional component as a subroutine. Also, the functional components are not limited to implementation by software and may alternatively be implemented by hardware such as an IC (integrated circuit) or a FPGA (field programmable gate array), for example.

The sample spectrum acquisition unit 30 acquires, from the mass spectrometer 100 via the interface device 20, for example, a sample spectrum S, and stores the acquired sample spectrum S in the memory device 18. Note that the sample spectrum S acquired from the mass spectrometer 100 in advance may be stored in the auxiliary storage device 16, and the stored data may be retrieved and loaded in the memory device 18, for example.

The auxiliary storage device 16 stores the spectrum library 16A having a plurality of reference spectra $S^*_j$ of a plurality of known substances j registered therein. The plurality of reference spectra $S^*_j$ are to be compared with the sample spectra S.

The sample substance may be a single substance or a mixed substance. Similarly, the known substance may be a single substance or a mixed substance. However, the known substance is preferably a simpler compound compared to the sample substance. That is, the sample spectra S may be composite data of a plurality of mass spectra, and the reference spectra S*$_j$ may be simpler data that may be included in the sample spectra S. The sample spectrum S and the reference spectra S*$_j$ may have a relationship similar to that of the first embodiment as illustrated in FIG. 5, for example.

[Individual Spectrum Similarity]

Calculation of the individual spectrum similarity in the present embodiment may be similar to the first embodiment so that descriptions thereof are omitted. Note, however, that in the present embodiment, the sample spectrum S and the reference spectra S*$_j$ do not necessarily have to be time series data. Accordingly, the individual spectrum similarity may be represented as (S, S*$_j$).

[Residual Spectrum Generation]

Figure 17:
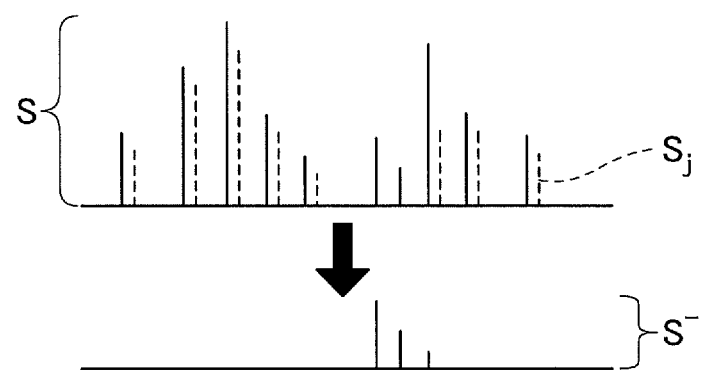
FIG. 17 illustrates how a residual spectrum is generated by subtracting a reference spectrum from a sample spectrum.

The residual spectrum generation unit 38 generates a residual spectrum S$^-$ by subtracting from the sample spectrum S a reference spectrum S*$_j$ for which a high individual spectrum similarity (S, S*$_j$) has been calculated by the individual spectrum calculation unit 32. FIG. 17 illustrates how the residual spectrum S$^-$ is generated by subtracting the reference spectra S*$_j$ from the sample spectrum S.

Note that in subtracting the reference spectra S*$_j$, some type of normalization process such as normalizing the maximum value is preferably applied.

The analysis device 2 of the present embodiment replaces the sample spectrum S with the generated residual spectrum S$^-$ and repeatedly performs the processes of the individual spectrum similarity calculation unit 32 and the residual spectrum generation unit 38. In a case where an individual spectrum similarity calculated with respect to the residual spectrum S$^-$ is improved compared to that calculated before subtraction of the reference spectrum S*$_j$, the individual spectrum similarity is updated. Such a loop process is iteratively performed until reaching a specified number of times corresponding to an upper limit or until no improvement of the individual spectrum similarity occurs.

Figure 18A:
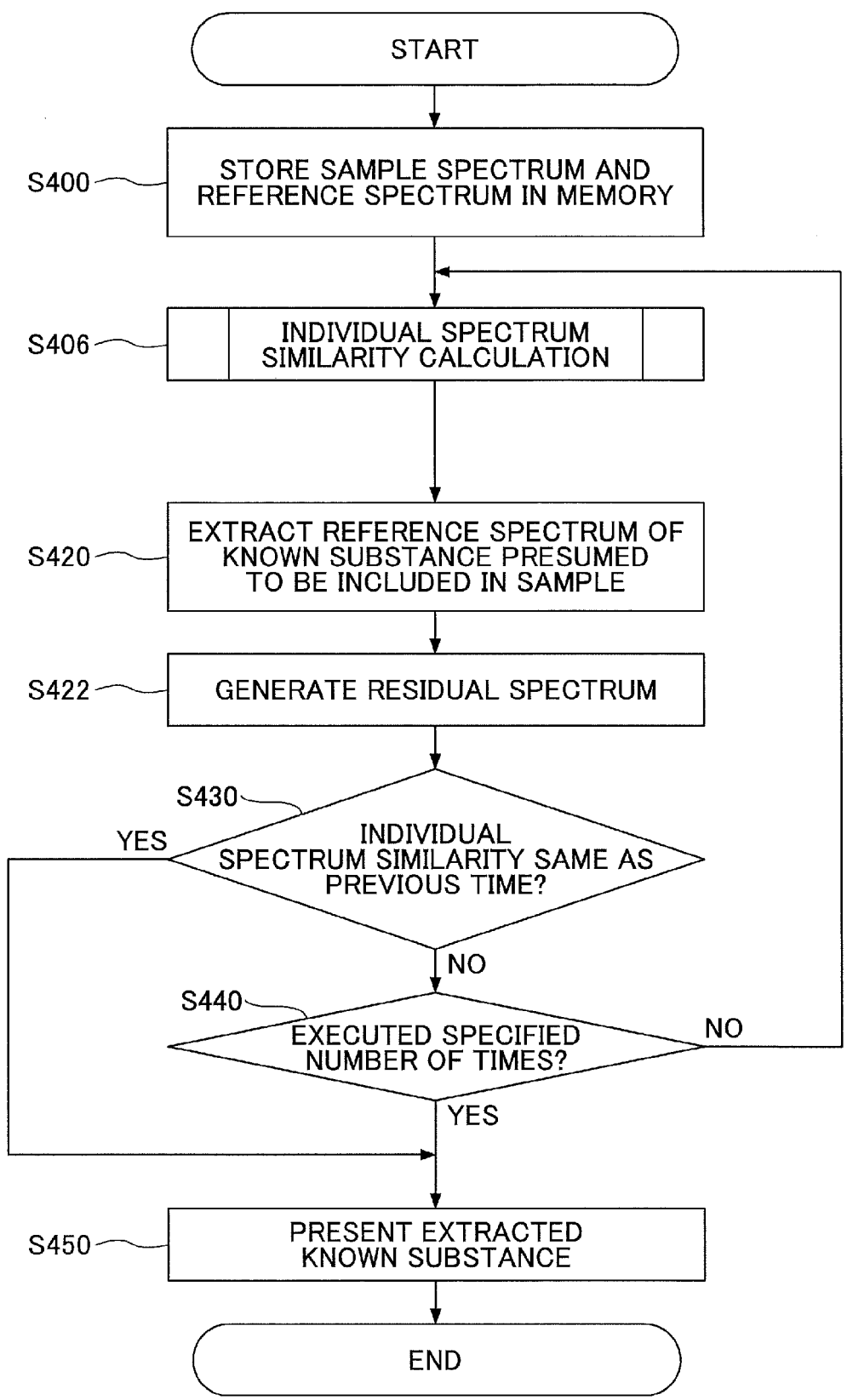
FIG. 18A is a flowchart illustrating process steps executed by the analysis device of the second embodiment.
Figure 18B:
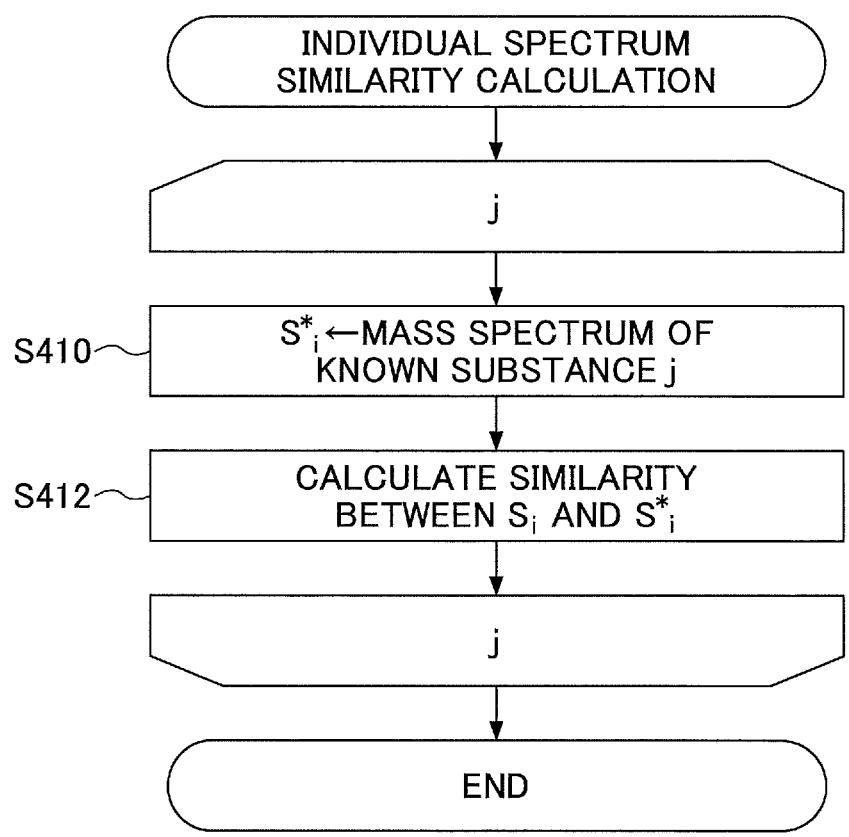
FIG. 18B is a flowchart illustrating a process flow for individual spectrum similarity calculation.

FIG. 18A is a flowchart illustrating exemplary process steps executed by the analysis device 2 according to the second embodiment.

First, the sample spectrum S is stored in the memory device 18, and likewise, the plurality of reference spectra S*$_j$ are stored in the memory device 18 (step S400). Note that the spectra data do not necessarily have to be loaded in the memory device 18, but instead, the spectra data stored in the auxiliary storage device 16 may be used, for example.

Next, individual spectrum similarity calculation is performed with respect to the sample spectrum S (step S406). FIG. 18A is a flowchart illustrating a process flow of the individual spectrum similarity calculation.

In the individual spectrum similarity calculation, process steps S410 and S412 are performed with respect to each of the plurality of reference spectra S*$_j$ (where j represents the number of known substances). In step S410, the mass spectrum of the j$^{th}$ known substance is extracted as reference spectrum S*$_j$ from the plurality of reference spectra. Then, in step S412, the individual spectrum similarity (S, S*$_j$) between the sample spectrum S and the reference spectrum S*$_j$ is calculated.

After the individual spectrum similarities (S, S*$_j$) are calculated with respect to the plurality of plurality of reference spectra S*$_j$, they may each be compared with a threshold value, for example, to extract a reference spectrum S*$_j$ of a known substance presumed to be included in the sample (step S420). The extracted reference spectrum S*$_j$ is then subtracted from the sample spectrum S (or residual spectrum S$^-$ in the case where the residual spectrum S$^-$ has already been generated) to generate the residual spectrum S$^-$ (step S422).

Then, a determination is made as to whether all the individual spectrum similarities (S, S*$_j$) calculated in step S412 are the same values as those previously calculated (step S430). If all the individual spectrum similarities (S, S*$_j$) calculated in step S412 are the same values as those previously calculated, the known substances included in the sample are identified from the reference spectra S*$_j$ extracted in step S420, and the information is presented to the user (step S450) after which the present process flow is ended.

On the other hand, in a case where not all the individual spectrum similarities (S, S*$_j$) calculated in step S412 are the same values as those previously calculated, a determination is made as to whether the loop process of steps S406-S440 has been performed the specified number of times or more (step S440). If the loop process of steps S406-S440 has been performed the specified number of times or more, the known substances included in the sample are identified from the reference spectra S*$_j$ extracted in step S420, and the information is presented to the user (step S450) after which the present process flow is ended.

If negative determinations are obtained in both steps S430 and S440, the process goes back to step S406.

By performing the above process, an accurate analysis may be made as to whether each of a plurality of reference spectra S*$_j$ are included in a sample spectrum including a plurality of components.

[Summary]

As can be appreciated from the above descriptions, by using the analysis device 2 of the present embodiment, a mass spectrum including a plurality of components may be analyzed and used for identifying a sample substance.

<Third Embodiment>

In the following, an analysis device 3 according to a third embodiment is described with reference to the accompanying drawings.

[Basic Configuration]

The basic configuration of the analysis device 3 of the present embodiment may be identical to that of the first embodiment as illustrated in FIG. 1 or 2. Note that in the third embodiment, the mass spectrometer 100 may be a LC/MS (liquid chromatography mass spectrometer), for example. In the LC/MS, a plurality of sample spectra S$_i$ may be obtained through gradient analysis, for example. That is, the LC/MS may obtain time series data acquired a plurality of times over a course of time during which environmental conditions are changed.

In gradient analysis, an intensity of a substance is measured through HPCL (high-performance liquid chromatography) using two pumps and two solvents (mobile phase). By establishing ratios of the two solvents and changing the ratios over time, a sample substance may be separated into components. For example, the following mobile phase conditions may be used in implementing gradient analysis. Water/formic acid (1000:1, v/v) is used as solvent A, and acetonitrile/formic acid (1000:1, v/v) is used as solvent B. Separation is first be performed through gradient elution using a mixture of solvent A and solvent B. In this process, the concentration of solvent B is set to 30% from the start of measurement until one minute elapses, and after one minute, the concentration of solvent B is increased to 100% and measurement is performed up to six minutes. Then, separation is performed through linear gradient elution for ten minutes using a mixture of solvent A and solvent B. In this process, the concentration of solvent B is increased from 40% to 50%. Measurement conditions of the LC/MS may be as follows, for example. Column: ODS column 2.1×50 mm; particle diameter: 1.7 µm; column temperature: 40° C.; flow rate: 0.2 mL/min; MS: ESI (positive ion detection mode).

[Functional Configuration of Analysis Device]

Figure 20:
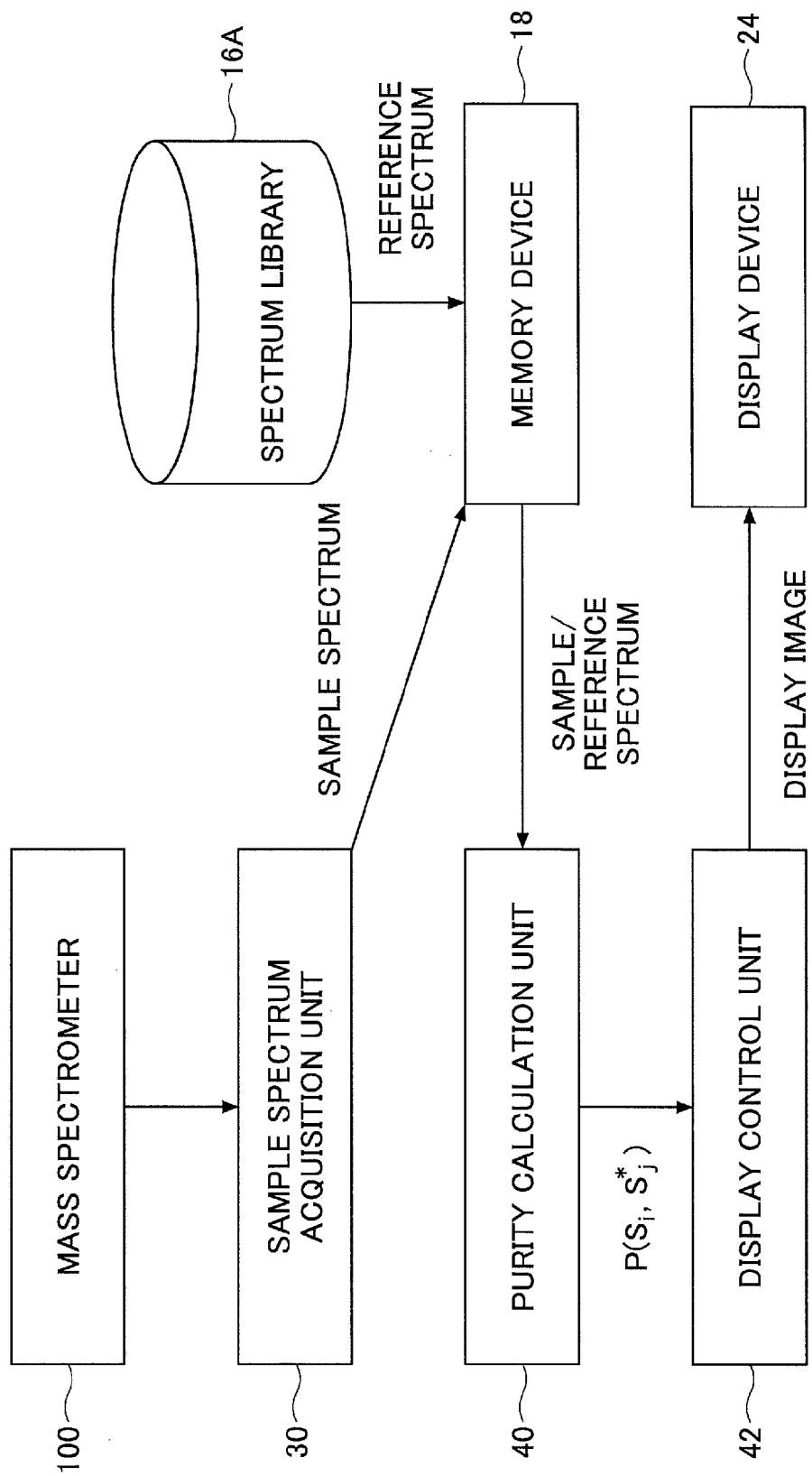
FIG. 20 illustrates an exemplary functional configuration of an analysis device according to a third embodiment of the present invention.

FIG. 20 illustrates a functional configuration of the analysis device 3 of the present embodiment. The analysis device 3 includes the sample spectrum acquisition unit 30, a purity calculation unit 40, and a display control unit 42.

The above functional components may be implemented by the CPU 10 executing program software stored in the auxiliary storage device 16, for example. Note that the functional components do not necessarily have to be implemented by separate programs. For example, one of the functional components may be called by another functional component as a subroutine. Also, the functional components are not limited to implementation by software and may alternatively implemented by hardware such as an IC (integrated circuit) or a FPGA (field programmable gate array), for example.

The sample spectrum acquisition unit 30 acquires, from the mass spectrometer 100 via the interface device 20, for example, a plurality of sample spectra $S_i$, and stores the acquired sample spectra $S_i$ in the memory device 18. Note that sample spectra $S_i$ acquired from the mass spectrometer 100 in advance may be stored in the auxiliary storage device 16, and the stored data may be retrieved and loaded in the memory device 18, for example.

The plurality of sample spectra $S_i$ correspond to time series data obtained by the mass spectrometer 100 a plurality of times over a course of time during which environmental conditions such as the temperature and the pressure are changed. The index "i" (i=1~n) of the sample spectra $S_i$ represents the sequential order of the spectrum data; namely, the number of times the spectrum data has been obtained.

The auxiliary storage device 16 stores the spectrum library 16A having reference spectra $S^*_j$ of a plurality of known substances j registered therein. The reference spectra $S^*_j$ are compared with the sample spectra $S_i$.

The reference spectra $S^*_j$ may correspond to spectrum data measured for a plurality of known substances j, for example. The reference spectra $S^*_j$ preferably represent spectrum data of substances indicating little or no change over time (i.e., not a very complex compound).

The sample substance and the known substances may be a single substance or a mixed substance.

The purity calculation unit 40 calculates, with respect to each combination of a sample spectrum $S_i$ of the plurality of sample spectra and a reference spectrum $S^*_j$ of the plurality of reference spectra, the purity $P(S_i, S^*_j)$ of the component represented by the reference spectrum $S^*_j$ within the sample.

Specifically, the purity calculation unit 40 extracts a maximum intensity of the reference spectrum $S^*_j$ at the m/z equal to or within a certain tolerance range of the m/z forming a peak in the sample spectrum $S_i$ and generates vector data I* of the same degree as the vector data I of the sample spectrum $S_i$.

Figure 21:
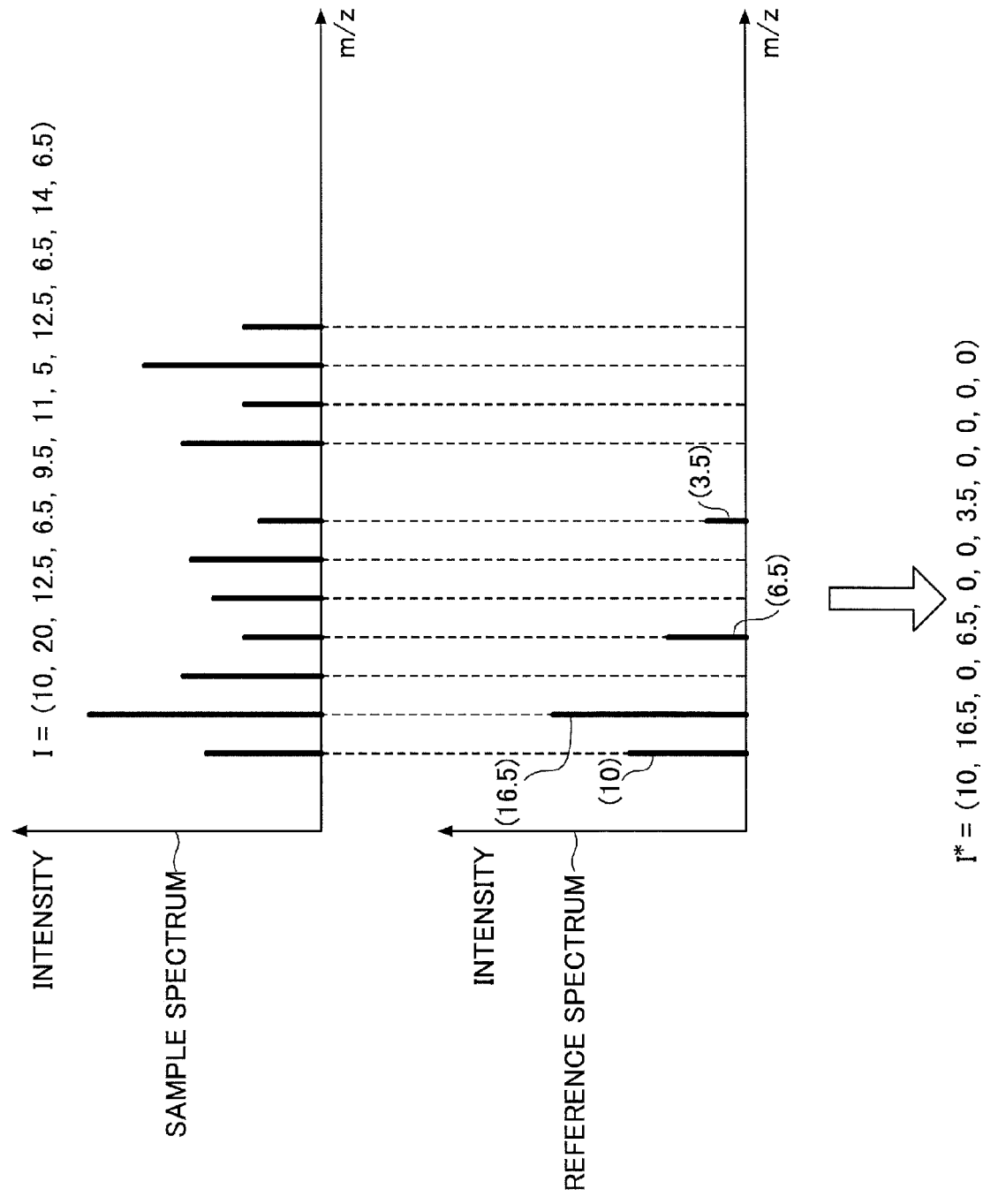
FIG. 21 illustrates how vector data of the same degree as vector data of a sample spectrum is generated by extracting a maximum intensity of a reference spectrum at a m/z equal to or within a certain tolerance range of a m/z forming a peak in the sample spectrum.

FIG. 21 illustrates how vector data I* of the same degree as the vector data I of the sample spectrum $S_i$ is generated by extracting the maximum intensity of the reference spectrum $S^*_j$ at the m/z equal to or within a certain tolerance range of the m/z forming a peak in the sample spectrum $S_i$. In a case where the reference spectrum $S^*_j$ does not have a peak at the m/z equal to or within a certain tolerance range of the m/z forming a peak in the sample spectrum $S_i$, the purity calculation unit 40 assigns the value zero (0) to the corresponding component of the vector data I*. In FIG. 21, the intensities at the m/z forming peaks in the reference spectrum $S^*_j$ are (10, 16.5, 6.5, 3.5) and zero (0) is assigned to components corresponding to the m/z forming peaks in the sample spectrum $S_i$ but not forming peaks in the reference spectrum $S^*_j$. In this way, the vector data I*=(10, 16.5, 0, 6.5, 0, 0, 3.5, 0, 0, 0, 0) is obtained.

Then, the purity calculation unit 40 calculates the purity $P(S_i, S^*_j)$ with respect to each combination of the sample spectrum $S_i$ and the reference spectrum $S^*_j$ based on the following equation (10). Note that in equation (10), $I_m$ represents the $m^{th}$ component of the vector data I, and $I^*_m$ represents the $m^{th}$ component of the vector data I*.

$$P(S_i, S^*_j) = \frac{(I, I^*)}{\|I\| \cdot \|I^*\|} = \frac{\sum (I_m \cdot I^*_m)}{\sqrt{\sum I_m^2} \cdot \sqrt{\sum I_m^{*2}}} \quad (10)$$

Note that the method of calculating the purity $P(S_i, S^*_j)$ is not limited to the above method. For example, the Pearson product-moment correlation coefficient may be used to obtain the purity $P(S_i, S^*_j)$. The following equation (11) represents a computing equation in a case where the Pearson product-moment correlation coefficient is used.

$$P(S_i, S^*_j) = \frac{\sum (I_m - \bar{I}) \cdot \sum (I^*_m - \bar{I^*})}{\sqrt{\sum (I_m - \bar{I})^2} \cdot \sqrt{\sum (I^*_m - \bar{I^*})^2}} \quad (11)$$

The display control unit 42 prompts the display device 24 to display all or part of the purity P calculated for a user-selected reference spectrum S*j or an automatically-selected reference spectrum S*j in association with the measurement timings (measurement time) of the sample spectrum. That is, the display control unit 42 prompts the display device 24 to display a temporal change in the purity P for the user-selected or automatically-selected reference spectrum $S^*_j$ (i.e., the purity P at each measurement timing) in conjunction with a temporal change in a total ion current chromatogram (TIC) of the sample substance, for example, to enable their comparison. The total ion current chromatogram (TIC) represents the summed intensity of ions at each measurement timing.

Figure 22:
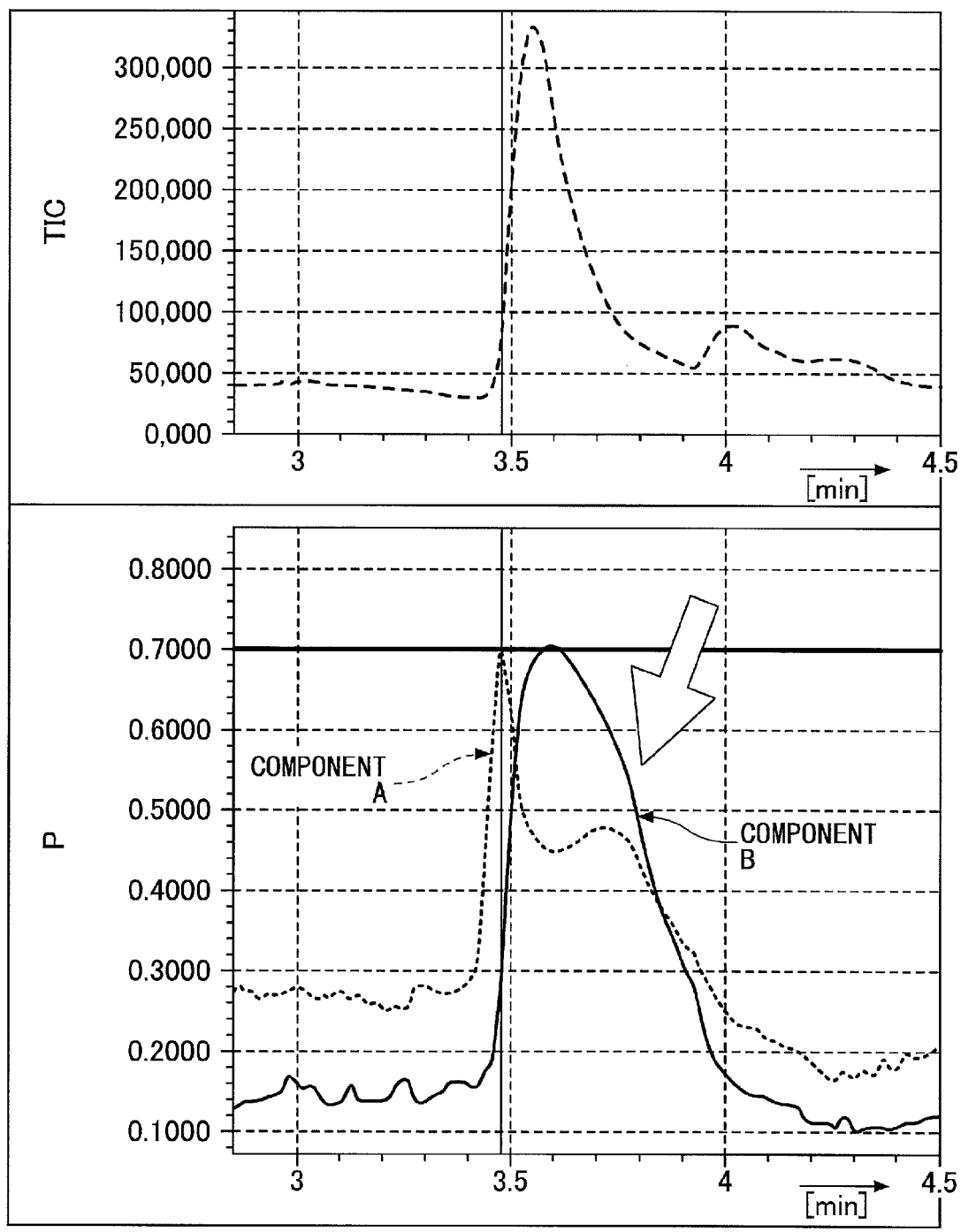
FIG. 22 illustrates an exemplary display screen generated by a display control unit.
Figure 23:
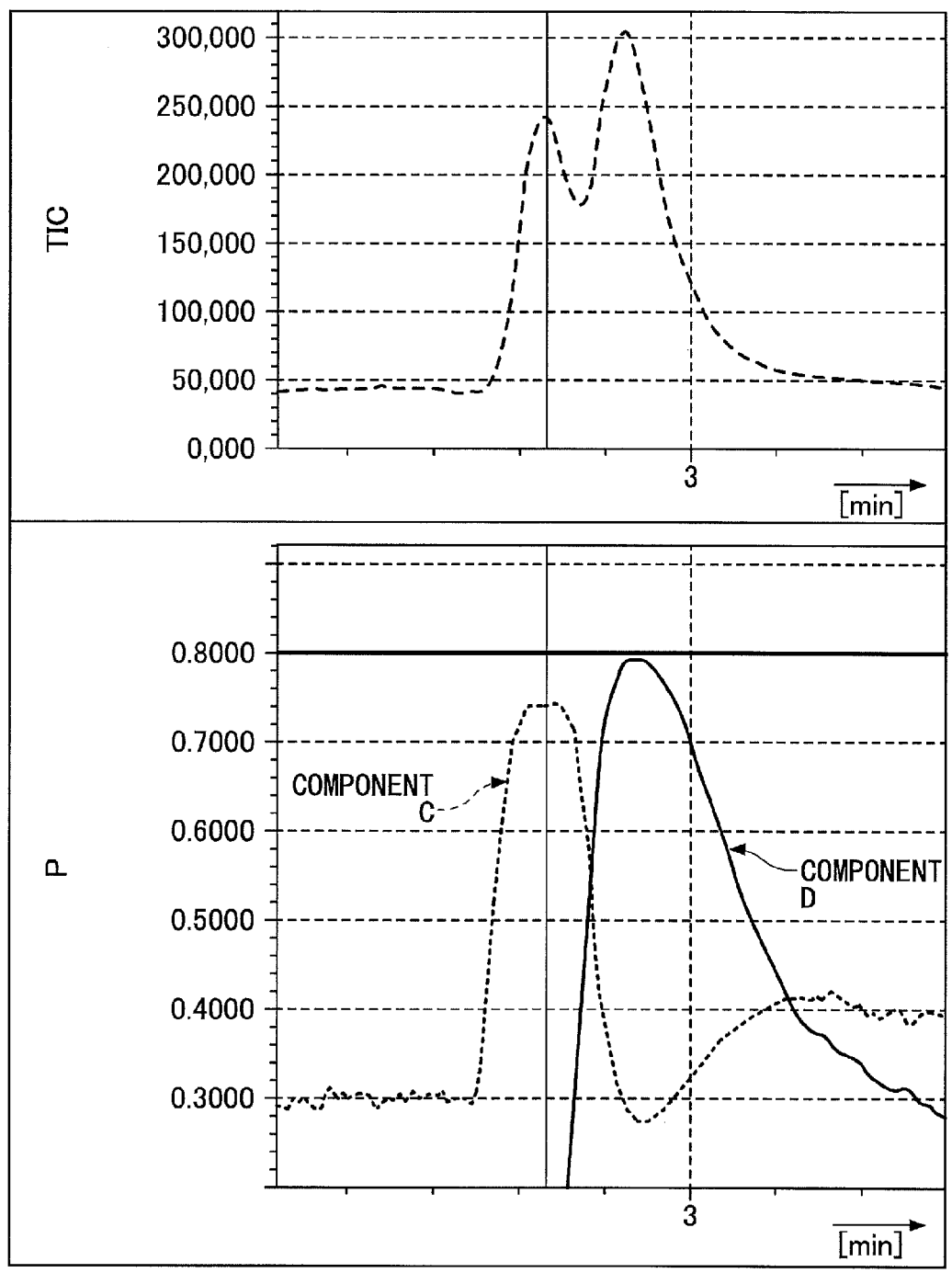
FIG. 23 illustrates another exemplary display screen generated by the display control unit.
Figure 24:
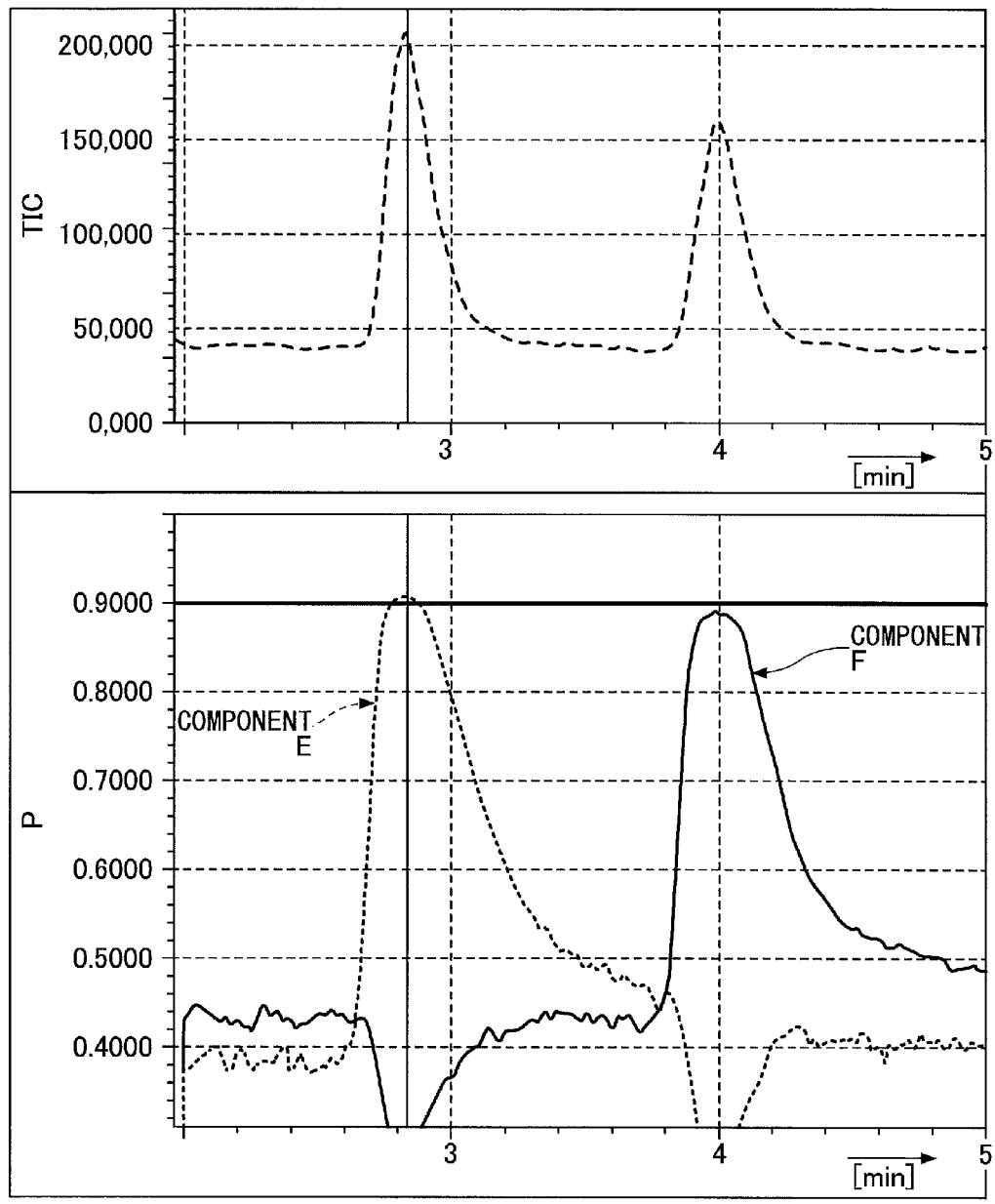
FIG. 24 illustrates another exemplary display screen generated by the display control unit.

FIGS. 22-24 illustrate exemplary display screens generated by the display control unit 42. Note that FIGS. 22-24 illustrate exemplary data obtained in a case where (1) an acetonitrile solution of Dimethyl Phthalate and (100 ppm) and Ethyl Paraben (500 ppm); and (2) an acetonitrile solution of Dimethyl Phthalate (20 ppm) and Propyl Paraben (100 ppm) were used as sample substances.

FIG. 22 illustrates a screen displaying a temporal change in a total ion current chromatogram (TIC) of a sample substance containing component A and component B (see upper graph of FIG. 22) and the purity P for the component A and the purity P for the component B (see lower graph of FIG. 22). As illustrated in FIG. 22, when component A and component B are separated under environmental conditions as described above, their measurement timings are relatively close, and as a result, the timings at which their purity P reach their peaks are also relatively close. Accordingly, it cannot be perceived only from the total ion current chromatogram (TIC) of the sample substance that the above two components are included in the sample substance, and the peak value of the purity P for component A and the peak value of the purity P for component B are merely around 0.7.

FIG. 23 illustrates a screen displaying a temporal change in a total ion current chromatogram (TIC) of a sample substance containing component C and component D (see upper graph of FIG. 23) and the purity P for the component C and the purity P for the component D (see lower graph of FIG. 23). As illustrated in FIG. 23, when component C and component D are separated under environmental conditions as described above, their measurement timings are farther apart compared to component A and component B, and as a result, the timings at which their purity P reach their peaks are also separated farther away from each other compared to FIG. 22. Accordingly, it can be perceived from the total ion current chromatogram (TIC) of the sample substance that the above two components are included in the sample substance, and the peak value of the purity P for component C and the peak value of the purity P for component C are around 0.8.

FIG. 24 illustrates a screen displaying a temporal change in a total ion current chromatogram (TIC) of a sample substance containing component E and component F (see upper graph of FIG. 24) and the purity P for the component E and the purity P for the component F (see lower graph of FIG. 23). As illustrated in FIG. 24, when component E and component F are separated under environmental conditions as described above, their measurement timings are clearly separated, and as a result, the timings at which their purity P reach their peaks are also separated farther away from each other compared to FIGS. 22 and 23. Accordingly, it can be clearly perceived from the total ion current chromatogram (TIC) of the sample substance that the above two components are included in the sample substance, and the peak value of the purity P for component E and the peak value of the purity P for component F reach up to around 0.9.

Figure 25:
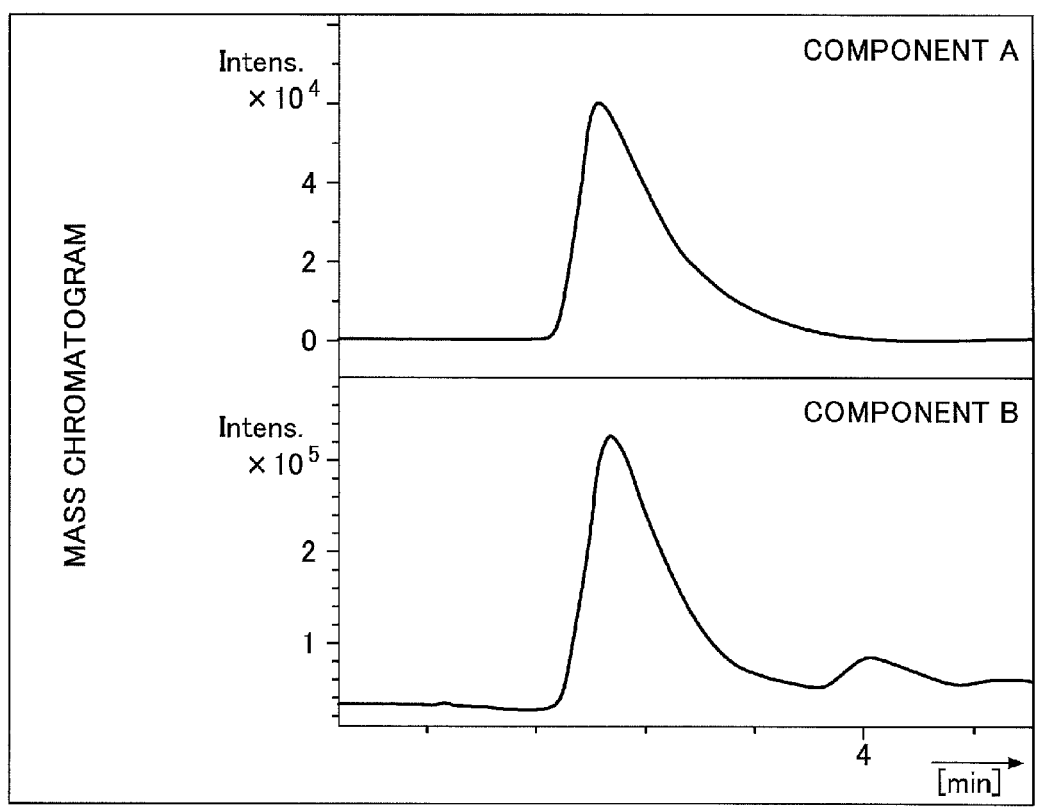
FIG. 25 illustrates mass chromatograms of components A and B.

By displaying the temporal change in the purity P, an analyzer (user) viewing the display may make various interpretations based on the displayed information. For example, when the peak value of the purity P for a component does not reach a very high value, the analyzer may understand that there may be another component at a similar measurement timing. Also, the purities P of a plurality of components reaching peak values at measurement timings within a close range are displayed along with the total ion current chromatogram (TIC) of the sample substance, the analyzer may understand that a peak of the total ion current chromatogram (TIC) of the sample substance is formed by a plurality of components. FIG. 25 illustrates mass chromatograms for component A and component B. When merely comparing the waveforms of FIG. 25 and the upper graph of FIG. 22, it cannot be determined whether the peak of the total ion current chromatogram (TIC) of the sample substance is formed by a plurality of components A and B. However, by displaying the purities P for the plurality of components A and B as in FIG. 22, the analyzer may determine that the total ion current chromatogram (TIC) of the sample substance is formed by a plurality of components A and B.

Further, by confirming that the measurement timing at which the purity P reaches a peak corresponds to or is close to the measurement timing at which the total ion current chromatogram (TIC) of the sample substance forms a peak, the analyzer may understand that the corresponding component is not merely a noise component. That is, even when the purity P of a component peaks at a measurement timing at which a total ion count value of the total ion current chromatogram (TIC) of the sample substance is relatively low, the analyzer may interpret this as the result of a component not constituting a major component of the sample substance matching the spectrum for the corresponding component.

Figure 26:
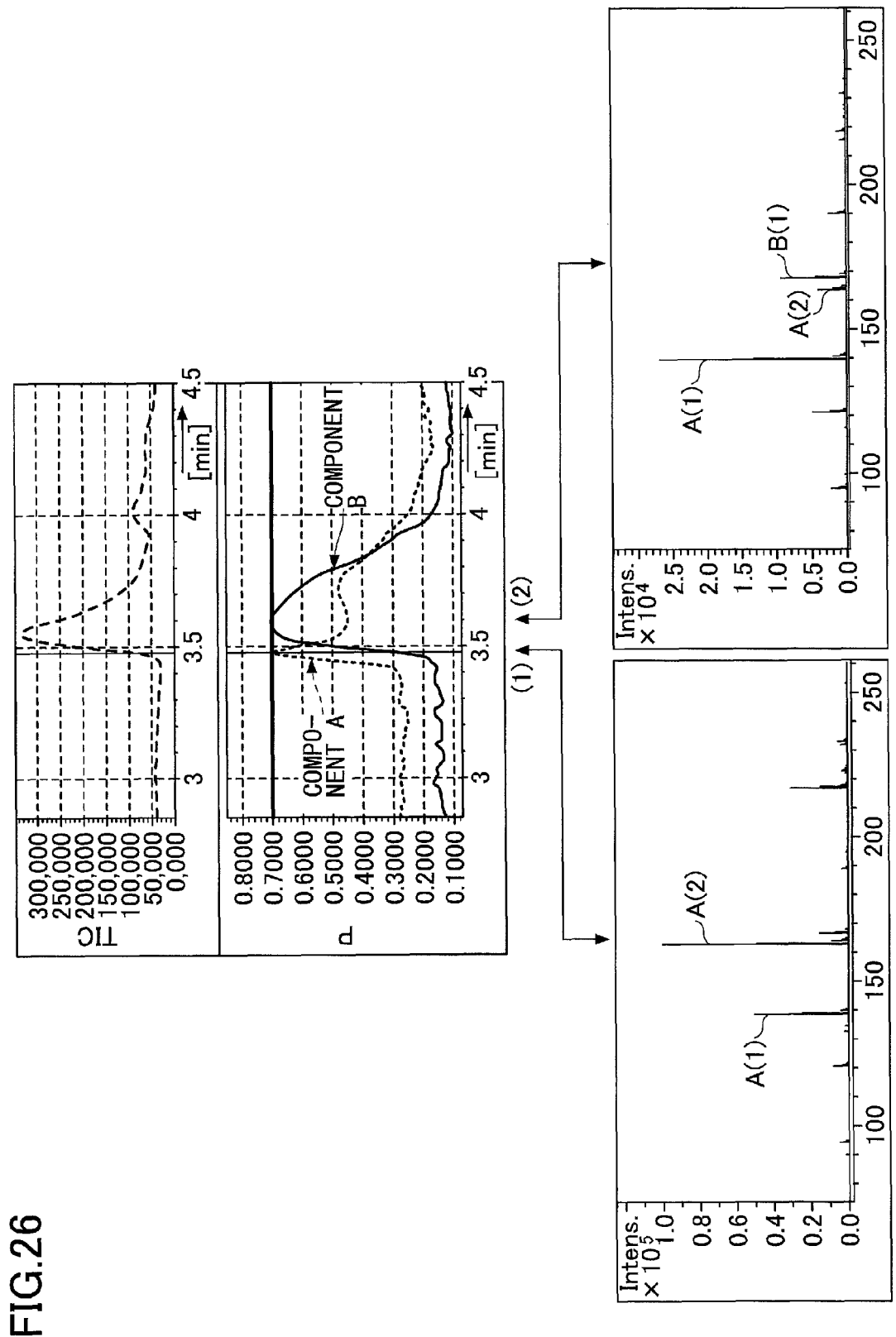
FIG. 26 illustrates mass spectra of a first measurement timing at which a purity value for component A reaches a peak and a second measurement timing at which a purity value for component B reaches a peak.

FIG. 26 illustrates mass spectra at a measurement timing (1) at which the purity P for component A reaches a peak and a measurement timing (2) at which the purity P for component B reaches a peak. In the mass spectrum at the lower left side of FIG. 26, the weights of spectra A(1) and A(2) for the substance derived from component A are high, and in the mass spectrum at the lower right side of FIG. 26, the weight of spectrum B(1) for the substance derived from component B is high. As can be appreciated, the purity P for each component may increase at a measurement timing according to an increase in the weight of the corresponding component.

[Flowchart]

FIG. 27 is a flowchart illustrating process steps executed by the analysis device 3 of the third embodiment.

First, the analysis device 3 stores in the spectrum library 16A reference spectra for one or more known substances measured at a plurality of measurement timings under predetermined environmental conditions (step S500).

Then, the analysis device 3 acquires sample spectra for a sample substance measured at a plurality of measurement timings under the same environmental conditions as above and stores the acquired sample spectra in the memory device 18 (step S502). Note that a temporal change in the total ion current chromatogram (TIC) of the sample substance is attached to the sample spectra acquired in step S502. Also, note that steps S500 and S502 do not necessarily have to be executed in the above order. That is, steps S500 and S502 may alternatively be executed in reverse order.

Then, the analysis device 3 selects a reference spectrum for which the purity P is to be calculated (step S504). The reference spectrum may be selected according to user operations or automatically. In the case of automatically selecting the reference spectrum, for example, the analysis device 3 may have functions similar to those of the first embodiment, and the analysis device 3 may be configured to select a reference spectrum with the highest overall similarity $U_j$.

Then, the purity calculation unit 40 of the analysis device 3 calculates the purity P for each combination of the selected reference spectrum and a sample spectrum of the plurality of sample spectra (step S506).

Then, the display control unit 42 of the analysis device 3 prompts the display device 24 to display the temporal change in the purity P calculated in step S506 and the temporal change in the total ion current chromatogram (TIC) of the sample substance such that the two may be compared with each other (step S508).

Thereafter, the analysis device 3 may select another reference spectrum automatically or according to user operations. The analysis device 3 may then display the temporal change in the purity P for the selected reference spectrum cumulatively or after deleting the previously displayed temporal change in the purity P, for example.

[Summary]

By using the analysis device 3 of the third embodiment as described above, the purity P may be displayed in association with the measurement timing, and in this way, information useful to the analyzer may be provided.

Although the present invention has been described above with respect to illustrative embodiments, the present invention is not limited to these embodiments and numerous variations and modifications may be made without departing from the scope of the present invention.

For example, in the above-described third embodiment, the reference spectrum $S^*_j$ preferably represents a substance with spectrum data indicating little or no change over time, and the reference spectrum $S^*_j$ corresponds to non-time-series data. However, in a case where the spectrum of a substance with spectrum data indicating substantial change over time is used as the reference spectrum, a plurality of reference spectra $S^*_{ji}$ corresponding to time series data may be used to calculate the purity P. Note that, as with the sample spectrum $S_i$, the index "i" (i=1~n) of the reference spectra $S^*_{ji}$ indicates the sequential order of the spectrum data; namely, the number of times the spectrum data has been obtained.

In the case of using the reference spectra $S^*_{ji}$, the analysis device 3 extracts, from the plurality of sample spectra $S_i$ and the plurality of reference spectra $S^*_{ji}$ for the selected known substance j, a combination of a sample spectrum $S_i$ and a reference spectrum $S^*_{ji}$ with the same measurement timing (i.e., having the same value for the index "i"), and calculates for each combination the purity $P(S_i, S^*_{ji})$ of the component represented by the reference spectrum $S^*_{ji}$ within the sample substance. Note that process steps performed thereafter may be identical to the above-described third embodiment. That is, all or a part of the calculated purity P is displayed at the display device 24 in association with the measurement timings (measurement time) of the sample spectra.

Note that there may be cases where the measurement timings and the number of measurements made for the sample substance and the known substances do not correspond. In such a case, slight differences may be disregarded (e.g., as long as the number of measurements are the same), or alternatively, a correction process such as time interpolation may be applied to match the measurement timings and the number of measurements, for example.

Although preferred embodiments of an analysis device, an analysis method, and a storage medium of the present invention have been described above, the present invention is not limited to these embodiments and numerous variations and modifications may be made without departing from the scope of the present invention.

The present application is based on and claims the benefit of priority of Japanese Patent Application No. 2011-191679 filed on Sep. 2, 2011 and Japanese Patent Application No. 2012-181749 filed on Aug. 20, 2012, the entire contents of which are herein incorporated by reference.

DESCRIPTION OF THE REFERENCE NUMERALS 1 analysis device
10 CPU
12 drive device
16 auxiliary storage device
16A spectrum library
18 memory device
20 interface device
22 input device
24 display device
30 sample spectrum acquisition unit
32 individual spectrum similarity calculation unit
34 overall similarity calculation unit
36 match determination unit
38 residual spectrum generation unit
40 purity calculation unit
42 display control unit
100 mass spectrometer
200 user

The invention claimed is:

1. An analysis device comprising:
a sample substance spectrum acquisition unit that acquires a plurality of sample substance spectra obtained a plurality of times for a same sample substance;
a storage unit that stores a plurality of reference spectra for a known substance;
a first evaluation value calculation unit that calculates a first evaluation value for a combination of a sample substance spectrum and a reference spectrum extracted from the plurality of sample substance spectra and the plurality of reference spectra, the first evaluation value representing a similarity between a peak intensity ratio of the reference spectrum and a peak intensity ratio of a portion of the sample substance spectrum corresponding to a peak in the reference spectrum; and
a second evaluation value calculation unit that calculates a second evaluation value representing a similarity between the sample substance and the known substance based on the first evaluation values for a plurality of the combinations.

2. The analysis device as claimed in claim 1, wherein
at least the plurality of sample substance spectra correspond to temporally ordered time series data; and
the second evaluation value calculation unit selects the combinations of the sample substance spectrum and the reference spectrum, in a manner not inconsistent with the temporal order, such that the combinations with comparatively high first evaluation values are selected, and calculates the second evaluation value by summing the first evaluation values for the selected combinations of the sample substance spectrum and the reference spectrum.

3. The analysis device as claimed in claim 2, wherein
the second evaluation value calculation unit selects the combinations of the sample substance spectrum and the reference spectrum based on matrix data generated by biaxially arranging the plurality of sample substance spectra and the plurality of reference spectra according to the temporal order and including the first evaluation values as data components, the second evaluation value calculation unit being configured to determine a shortest path on the matrix data from an earliest data component to a latest data component according to the temporal order corresponding to a path with a comparatively high data component total value, and select the combinations of the sample substance spectrum and the reference spectrum corresponding to the shortest path.

4. The analysis device as claimed in claim 2, wherein the temporal order corresponds to an order in which a mass spectrometer obtains spectrum data from at least one of the sample substance and the known substance under a varying environment.

5. An analysis device as claimed in claim 1, wherein the first evaluation value calculation unit extracts a mass-to-charge ratio (m/z) corresponding to a peak of the reference spectrum, and calculates the first evaluation value by obtaining a cosine of an angle formed by a first vector and a second vector, the first vector including an intensity of each peak in the reference spectrum as a component, and the second vector including an intensity at the extracted mass-to-charge ratio (m/z) in the sample substance spectrum as a component.

6. The analysis device as claimed in claim 1, further comprising:
a determination unit that recursively determines whether the sample substance includes the known substance based on a distribution of the second evaluation value.

7. An analysis device comprising:
a sample substance spectrum acquisition unit that acquires a sample substance spectrum for a sample substance;
a storage unit that stores a plurality of reference spectra for a plurality of known substances;
an evaluation value calculation unit that calculates an evaluation value representing a similarity between a peak intensity ratio of a reference spectrum of the plurality of reference spectra and a peak intensity of a portion of the sample substance spectrum corresponding to a peak in the reference spectrum; and a residual spectrum generation unit that generates a residual spectrum by subtracting from the sample substance spectrum the reference spectrum for which a comparatively high evaluation value is calculated by the evaluation value calculation unit;

wherein the sample substance spectrum is replaced by the residual spectrum generated by the residual spectrum generation unit and the evaluation value is calculated, after which a process of generating the residual spectrum and calculating the evaluation value is repeatedly executed.

8. An analysis method executed by a computer, the analysis method comprising:

a process of acquiring a plurality of sample substance spectra obtained a plurality of times for a same sample substance;

a process of calculating a first evaluation value for a combination of a sample substance spectrum and a reference spectrum extracted from the plurality of sample substance spectra and a plurality of reference spectra stored in a storage unit, the first evaluation value representing a similarity between a peak intensity ratio of the reference spectrum and a peak intensity ratio of a portion of the sample substance spectrum corresponding to a peak in the reference spectrum; and a process of calculating a second evaluation value representing a similarity between the sample substance and the known substance based on the first evaluation values for a plurality of the combinations.

9. An analysis method executed by a computer, the analysis method comprising:

a process of acquiring a sample substance spectrum for a sample substance;

a process of calculating an evaluation value representing a similarity between a peak intensity ratio of a reference spectrum of a plurality of reference spectra stored in a storage unit and a peak intensity of a portion of the sample substance spectrum corresponding to a peak in the reference spectrum; and a process of generating a residual spectrum by subtracting from the sample substance spectrum the reference spectrum for which a comparatively high evaluation value is calculated;

wherein the computer replaces the sample substance spectrum with the generated residual spectrum and calculates the evaluation value, and then repeatedly executes the processes of generating the residual spectrum and calculating the evaluation value.

10. A computer-readable medium having a computer program stored thereon that is executable by a computer, the computer program when executed causing the computer to perform:

a process of acquiring a plurality of sample substance spectra obtained a plurality of times for a same sample substance;

a process of calculating a first evaluation value for a combination of a sample substance spectrum and a reference spectrum extracted from the plurality of sample substance spectra and a plurality of reference spectra stored in a storage unit, the first evaluation value representing a similarity between a peak intensity ratio of the reference spectrum and a peak intensity ratio of a portion of the sample substance spectrum corresponding to a peak in the reference spectrum; and a process of calculating a second evaluation value representing a similarity between the sample substance and the known substance based on the first evaluation values for a plurality of the combinations.

11. A computer-readable medium having a computer program stored thereon that is executable by a computer, the computer program when executed causing the computer to perform:

a process of acquiring a sample substance spectrum for a sample substance;

a process of calculating an evaluation value representing a similarity between a peak intensity ratio of a reference spectrum of a plurality of reference spectra stored in a storage unit and a peak intensity of a portion of the sample substance spectrum corresponding to a peak in the reference spectrum; and a process of generating a residual spectrum by subtracting from the sample substance spectrum the reference spectrum for which a comparatively high evaluation value is calculated;

wherein the computer replaces the sample substance spectrum with the generated residual spectrum and calculates the evaluation value, and then repeatedly executes the processes of generating the residual spectrum and calculating the evaluation value.

12. An analysis device comprising:

a sample substance spectrum acquisition unit that acquires a plurality of sample substance spectra obtained at a plurality of measurement timings from a sample substance placed under a predetermined environment;

a storage unit that stores a reference spectrum obtained from a known substance;

an index value calculation unit that calculates an index value representing a proportion at which the known substance is included in the sample substance based on the sample substance spectra and the reference spectrum; and a display control unit that controls a display device to display the calculated index value in association with the measurement timings of the sample substance spectra.

13. The analysis device as claimed in claim 12, wherein the index value calculation unit calculates a plurality of the index values for a plurality of measurement timings; and the display control unit controls the display device to display an image that enables comparison between a temporal change in the calculated index value and a temporal change in an intensity sum of the sample substance spectra.

14. An analysis method executed by a computer, the analysis method comprising the steps of:

storing a reference spectrum obtained from a known substance in a storage unit;

acquiring a plurality of sample substance spectra obtained at a plurality of measurement timings from a sample substance placed under a-predetermined environmental conditions that are changed;

calculating an index value representing a proportion at which the known substance is included in the sample substance based on the sample substance spectra and the reference spectrum; and controlling a display device to display the calculated index value in association with the measurement timings of the sample substance spectra.

15. A computer-readable medium having a computer program stored thereon that is executable by a computer, the computer program when executed causing the computer to perform the steps of:

storing a reference spectrum obtained from a known substance in a storage unit;
acquiring a plurality of sample substance spectra obtained at a plurality of measurement timings from a sample substance placed under a-predetermined environmental conditions that are changed;
calculating an index value representing a proportion at which the known substance is included in the sample substance based on the sample substance spectra and the reference spectrum; and
controlling a display device to display the calculated index value in association with the measurement timings of the sample substance spectra.

* * * * *